(12) United States Patent
Merchant

(10) Patent No.: US 8,828,010 B2
(45) Date of Patent: Sep. 9, 2014

(54) METHOD AND APPARATUS FOR PERFORMING MULTIDIRECTIONAL TIBIAL TUBERCLE TRANSFERS

(75) Inventor: Alan C. Merchant, Los Altos, CA (US)

(73) Assignee: Kinamed, Inc., Camarillo, CA (US)

(*) Notice: Subject to any disclaimer, the term of this patent is extended or adjusted under 35 U.S.C. 154(b) by 208 days.

(21) Appl. No.: 13/347,493

(22) Filed: Jan. 10, 2012

(65) Prior Publication Data

US 2012/0184962 A1 Jul. 19, 2012

Related U.S. Application Data

(60) Provisional application No. 61/431,733, filed on Jan. 11, 2011.

(51) Int. Cl.
*A61B 17/56* (2006.01)
*A61B 17/15* (2006.01)

(52) U.S. Cl.
USPC ............................................ 606/87; 606/86 R

(58) Field of Classification Search
USPC ........................ 606/79, 82, 86 R, 87–89, 96
See application file for complete search history.

(56) References Cited

U.S. PATENT DOCUMENTS

| | | | |
|---|---|---|---|
| 5,620,448 | A | 4/1997 | Puddu |
| 6,008,433 | A | 12/1999 | Stone |
| 6,086,593 | A | 7/2000 | Bonutti |
| 6,203,546 | B1 | 3/2001 | MacMahon |
| 6,689,139 | B2 | 2/2004 | Horn |
| 6,796,986 | B2 | 9/2004 | Duffner |
| 6,823,871 | B2 | 11/2004 | Schmieding |
| 7,794,466 | B2 | 9/2010 | Merchant et al. |
| 2008/0015605 | A1* | 1/2008 | Collazo .......................... 606/87 |

* cited by examiner

*Primary Examiner* — Nicholas Woodall
*Assistant Examiner* — Larry E Waggle, Jr.
(74) *Attorney, Agent, or Firm* — Pandiscio & Pandiscio

(57) ABSTRACT

Apparatus for performing a multidirectional tibial tubercle transfer, comprising a jig for positioning against the anterior portion of the tibia, the jig comprising first and second guide surfaces which simultaneously converge towards one another as they extend distally down, and posteriorly towards, the tibia; a medial extender for attaching to the jig, wherein the medial extender comprises a third guide surface which is directed towards a point distal to the point of convergence of the first and second guide surfaces as the third guide surface extends distally down, and posteriorly towards, the tibia; and a lateral extender for attaching to the jig, wherein the lateral extender comprises a fourth guide surface which is directed towards a point distal to the point of convergence of the first and second guide surfaces as the fourth guide surface extends distally down, and posteriorly towards, the tibia.

5 Claims, 58 Drawing Sheets

METHOD AND APPARATUS FOR PERFORMING MULTIDIRECTIONAL TIBIAL TUBERCLE TRANSFERS

REFERENCE TO PENDING PRIOR PATENT APPLICATION

This patent application claims benefit of prior U.S. Provisional Patent Application Ser. No. 61/431,733, filed Jan. 11, 2011 by Alan C. Merchant for METHOD AND APPARATUS FOR PERFORMING MULTIDIRECTIONAL TIBIAL TUBERCLE TRANSFERS, which patent application is hereby incorporated herein by reference.

FIELD OF THE INVENTION

This invention relates to surgical methods and apparatus in general, and more particularly to surgical methods and apparatus for performing tibial tubercle transfers.

BACKGROUND OF THE INVENTION

In the field of orthopedic surgery, transferring the tibial tubercle is a well-recognized operative technique to correct the alignment of the extensor mechanism of the knee when that portion of the knee is found to be misaligned. This is traditionally done by moving the tibial tubercle from its current, non-optimum location to a more desirable location. The most common directions of transfer are medial and anteromedial, although other directions have been described in the literature as well.

Prior art approaches for transferring the tibial tubercle have generally proven to be problematic for a variety of reasons. Among other things, prior art approaches for transferring the tibial tubercle have generally proven to be (i) relatively complex and time-consuming to perform, (ii) less precise than desired, (iii) not highly reproducible from patient-to-patient and surgeon-to-surgeon, (iv) technique restrictive, and/or (v) procedurally invasive.

Thus there is a need for an improved method and apparatus for transferring the tibial tubercle, such that the transfer process is simpler and faster to perform, more precise, more highly reproducible from patient-to-patient and surgeon-to-surgeon, less technique restrictive, and/or less invasive than prior art techniques.

SUMMARY OF THE INVENTION

These and other objects are addressed by the present invention, which comprises an improved method and apparatus for transferring the tibial tubercle.

More particularly, in one form of the invention, there is provided apparatus for performing a multidirectional tibial tubercle transfer, comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and an extender for attaching to the jig, wherein the extender comprises a third guide surface, wherein the third guide surface simultaneously converges towards the point of convergence of the first and second guide surfaces of the jig as the third guide surface extends (i) distally down the tibia, and (ii) posteriorly towards the tibia;

wherein the extender comprises an arcuate slot, and further wherein the extender is attached to the jig by means of the arcuate slot.

In another form of the invention, there is provided apparatus for performing a multidirectional tibial tubercle transfer, comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and an extender for attaching to the jig, wherein the extender comprises a third guide surface, wherein the third guide surface simultaneously converges towards the point of convergence of the first and second guide surfaces of the jig as the third guide surface extends (i) distally down the tibia, and (ii) posteriorly towards the tibia;

wherein the extender comprises a slot, and further wherein the third guide surface defines a portion of the slot.

In another form of the invention, there is provided apparatus for performing a multidirectional tibial tubercle transfer, comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia;

a medial extender for attaching to the jig, wherein the medial extender comprises a third guide surface, wherein the third guide surface is directed towards a point distal to the point of convergence of the first and second guide surfaces of the jig as the third guide surface extends (i) distally down the tibia, and (ii) posteriorly towards the tibia; and a lateral extender for attaching to the jig, wherein the lateral extender comprises a fourth guide surface, wherein the fourth guide surface is directed towards a point distal to the point of convergence of the first and second guide surfaces of the jig as the fourth guide surface extends (i) distally down the tibia, and (ii) posteriorly towards the tibia.

In another form of the invention, there is provided apparatus for performing a multidirectional tibial tubercle transfer, comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and an extender for attaching to the jig, wherein the extender comprises a third guide surface and a fourth guide surface, wherein the third guide surface and the fourth guide surface simultaneously converge towards the point of convergence of the first and second guide surfaces of the jig as the third guide surface and the fourth guide surface extend (i) distally down the tibia, and (ii) posteriorly towards the tibia.

In another form of the invention, there is provided a method for performing a multidirectional tibial tubercle transfer, the method comprising:

providing apparatus comprising:
a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and
an extender for attaching to the jig, wherein the extender comprises a third guide surface, wherein the third guide surface simultaneously converges towards the point of convergence of the first and second guide surfaces of the jig as the third guide surface extends (i) distally down the tibia, and (ii) posteriorly towards the tibia;

wherein the extender comprises an arcuate slot, and further wherein the extender is attached to the jig by means of the arcuate slot;

making a first cut in the tibia;

aligning the first guide surface of the jig with the first cut in the tibia;

making a second cut in the tibia using the second guide surface of the jig; and making a third cut in the tibia using the third guide surface of the extender.

In another form of the invention, there is provided a method for performing a multidirectional tibial tubercle transfer, the method comprising:

providing apparatus comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and an extender for attaching to the jig, wherein the extender comprises a third guide surface, wherein the third guide surface simultaneously converges towards the point of convergence of the first and second guide surfaces of the jig as the third guide surface extends (i) distally down the tibia, and (ii) posteriorly towards the tibia;

wherein the extender comprises a slot, and further wherein the third guide surface defines a portion of the slot;

making a first cut in the tibia;

aligning the first guide surface of the jig with the first cut in the tibia;

making a second cut in the tibia using the second guide surface of the jig; and making a third cut in the tibia using the third guide surface of the extender.

In another form of the invention, there is provided a method for performing a multidirectional tibial tubercle transfer, the method comprising:

providing apparatus comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia;

a medial extender for attaching to the jig, wherein the medial extender comprises a third guide surface, wherein the third guide surface is directed towards a point distal to the point of convergence of the first and second guide surfaces of the jig as the third guide surface extends (i) distally down the tibia, and (ii) posteriorly towards the tibia; and a lateral extender for attaching to the jig, wherein the lateral extender comprises a fourth guide surface, wherein the fourth guide surface is directed towards a point distal to the point of convergence of the first and second guide surfaces of the jig as the fourth guide surface extends (i) distally down the tibia, and (ii) posteriorly towards the tibia;

determining if the jig is appropriately sized for the patient;

if it is determined that the jig is appropriately sized for the patient, making a first cut in the tibia, aligning the first guide surface of the jig with the first cut in the tibia, making a second cut in the tibia using the second guide surface of the jig, and making a third cut in the tibia using the third guide surface of the medial extender;

if it is determined that the jig is not appropriately sized for the patient, making a first cut in the tibia using the fourth guide surface of the lateral extender, making a second cut in the tibia using the third guide surface of the medial extender, and making a fourth cut in the tibia using the third guide surface of the medial extender.

In another form of the invention, there is provided a method for performing a multidirectional tibial tubercle transfer, the method comprising:

providing apparatus comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and an extender for attaching to the jig, wherein the extender comprises a third guide surface and a fourth guide surface, wherein the third guide surface and the fourth guide surface simultaneously converge towards the point of convergence of the first and second guide surfaces of the jig as the third guide surface and the fourth guide surface extend (i) distally down the tibia, and (ii) posteriorly towards the tibia;

making a first cut in the tibia;

aligning the first guide surface of the jig with the first cut in the tibia;

making a second cut in the tibia using the second guide surface of the jig; and making a third cut in the tibia using the third guide surface of the extender.

In another form of the invention, there is provided a method for performing a multidirectional tibial tubercle transfer, the method comprising:

providing apparatus comprising:

a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and an extender for attaching to the jig, wherein the extender comprises a third guide surface and a fourth guide surface, wherein the third guide surface and the fourth guide surface simultaneously converge towards a point distal to the point of convergence of the first and second guide surfaces of the jig as the third guide surface and the fourth guide surface extend (i) distally down the tibia, and (ii) posteriorly towards the tibia;

making a first cut in the tibia using the fourth guide surface of the extender;

making a second cut in the tibia using the third guide surface of the extender; and making a third cut in the tibia using the third guide surface of the extender.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like elements and further wherein.

DETAILED DESCRIPTION OF THE PREFERRED EMBODIMENTS

Tibial Tubercle Transfer Procedure In General

The present invention comprises an improved method and apparatus for transferring the tibial tubercle. Among other things, it provides an improved, more precisely controllable, multi-directional, and independently variable tibial tubercle transfer technique. The present invention is intended to be used in performing a patellar tendon re-alignment by moving the tibial tubercle medially, antero-medially, laterally, anterolaterally, distally, antero-distally, proximally, antero-proximally, or any combination thereof, as appropriate for a specific patient.

For clarity of explanation, the present invention will hereinafter be discussed in the context of a medial transfer, although it will be appreciated that other transfer directions are also possible with the present invention.

Several factors are important to performing an ideal, anatomically-preferred tibial tubercle transfer: (a) the surgeon should be able to move the tibial tubercle wedge (into which the patellar tendon is inserted) a precise distance medially or laterally, etc.; and (b) the surgeon should be able to move the tibial tubercle wedge a precise distance anteriorly. To this end, the present invention provides the surgeon with instrumentation in the form of cutting guides that attach to the tibial tubercle and allow the surgeon to make precise cuts into the tibia with oscillating saw blades and osteotomes. The bone wedges produced by these cuts may then be precisely and accurately transposed within the tibia so as to re-align the patellar tendon laterally or medially and, if desired, the wedge associated with the patellar tendon insertion may be positioned anteriorly. The present invention provides various forms of instrumentation for effecting the various bone cuts used for the tibial tubercle transfer.

Sidearm Construction

Figure 1:
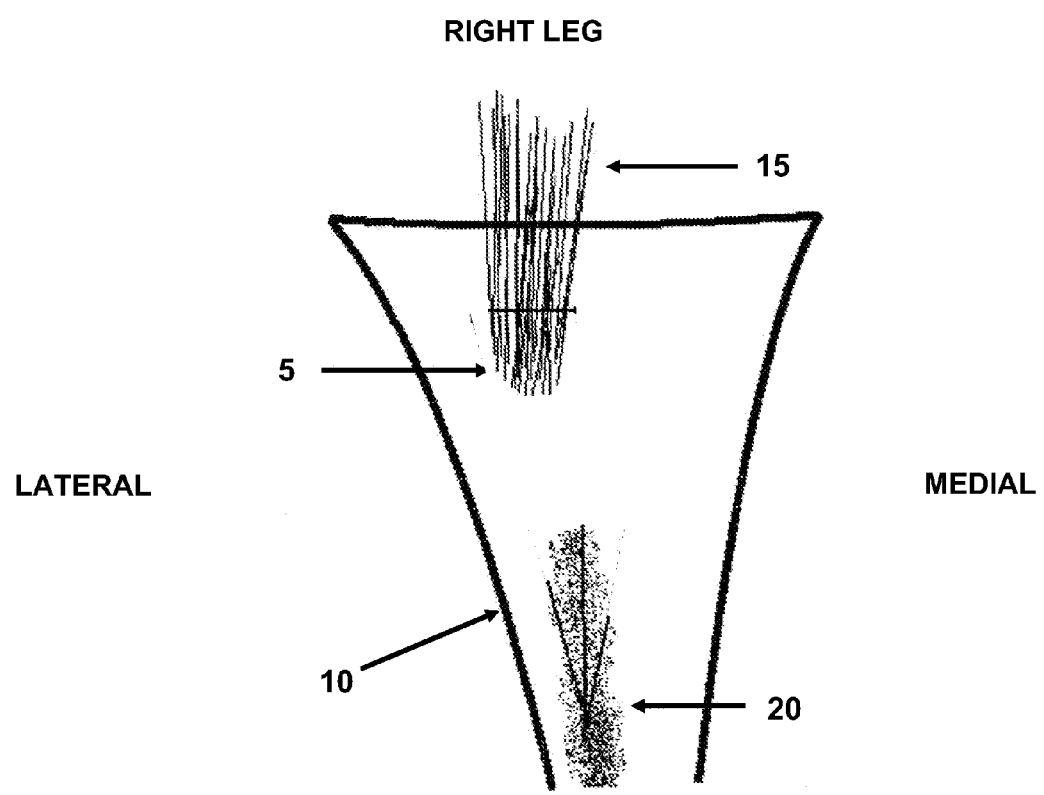
FIGS. 1-22 are a series of schematic views showing the novel tibial tubercle transfer procedure of the present invention being effected using one novel form of apparatus.
Figure 2:
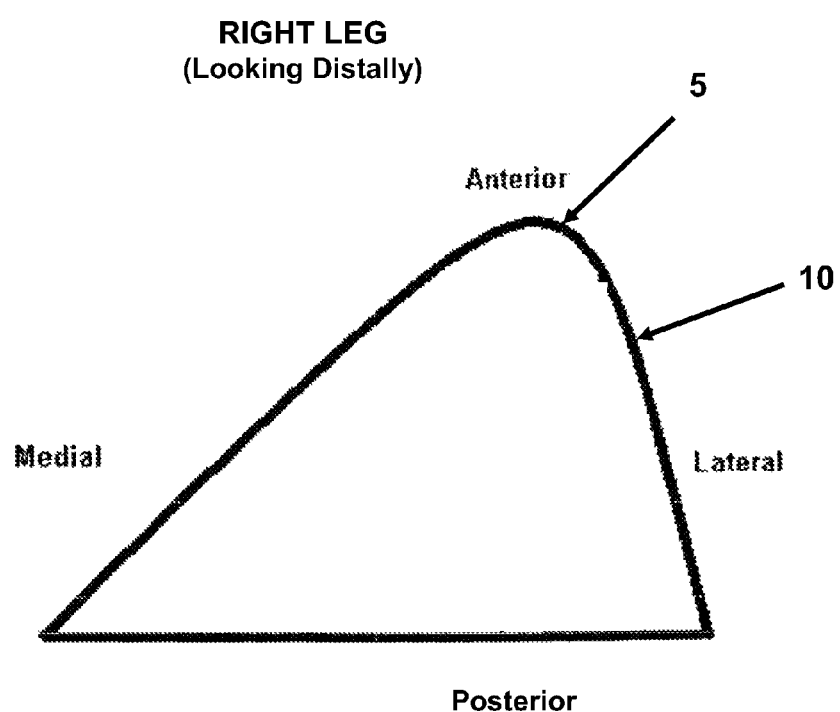

In one form of the invention, and looking first at FIGS. 1 and 2, the tibial tubercle 5 of tibia 10 is first exposed through a small incision in the skin (not shown). Note how the insertion point of patellar tendon 15 into tibial tubercle 5 lies above (i.e., proximal to) the tibial crest 20 of tibia 10.

Figure 3:
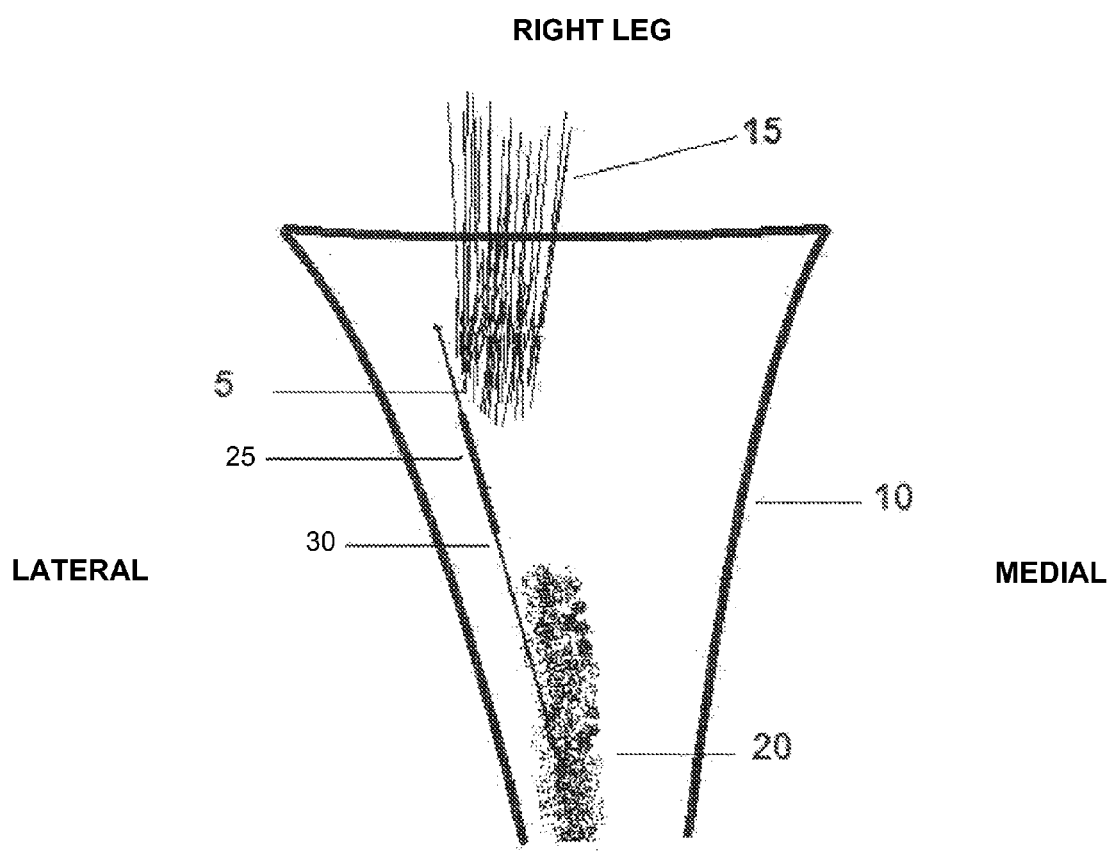
Figure 4:
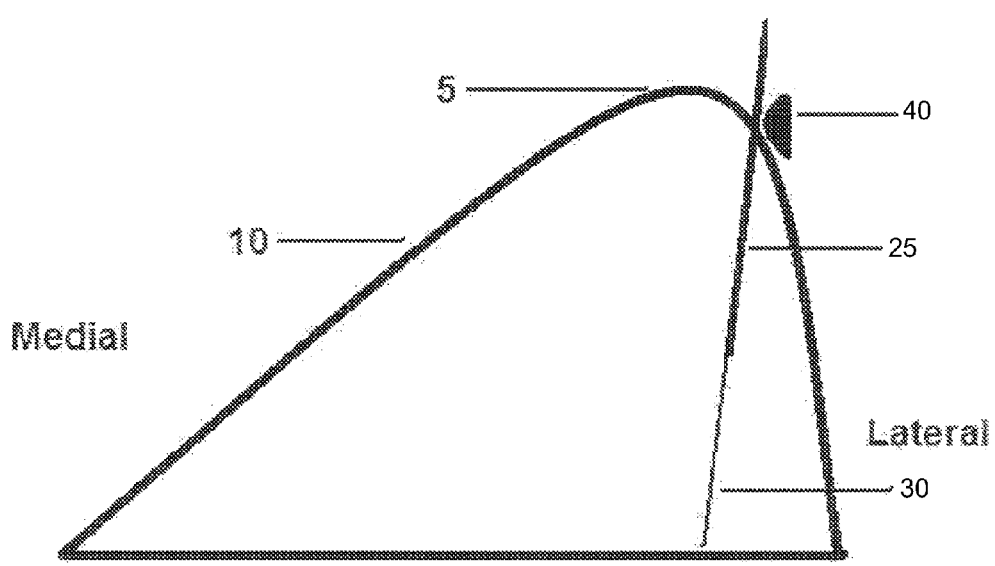
Figure 5:
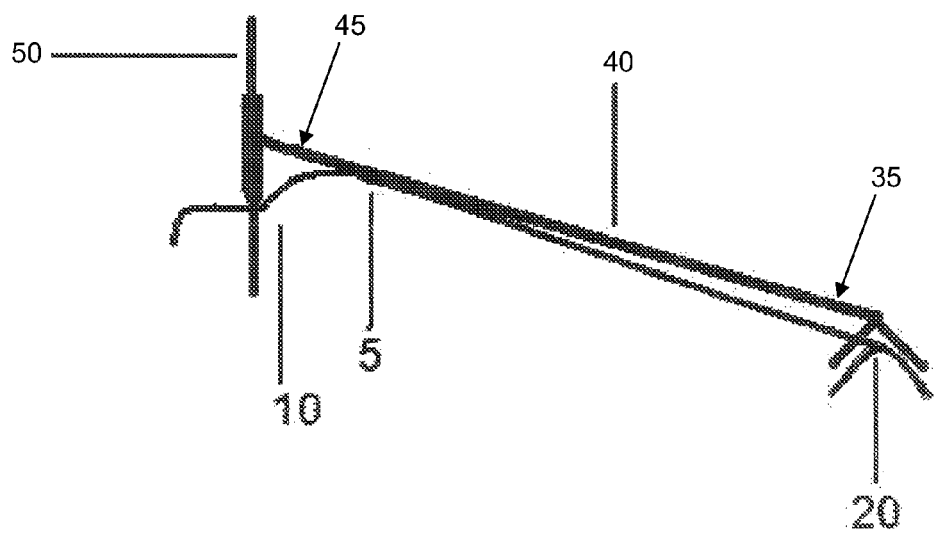

Next, and looking now at FIGS. 3-5, an end-cutting oscillating bone saw (not shown) comprising a saw blade 25 is used to make a short plunge-cut 30 at the lateral edge of tibial tubercle 5, directed posteromedially to avoid cutting the lateral tibial cortex and aligned to meet anterior tibial crest 20 of tibia 10 at a point distal to tibial tubercle 5. Saw blade 25 is detached from the bone saw, leaving the saw blade in cut 30. The distal end 35 of a lateral saw guide 40 is positioned over tibial crest 20, the lateral saw guide bar is brought up against saw blade 25, and the proximal end 45 of lateral saw guide 40 is secured to tibia 10, e.g., with a fixation pin 50. With lateral saw guide 40 thus fixed to the proximal tibia 10, saw blade 25 is removed from the bone and re-attached to the bone saw, whereupon the first cut 30 is completed.

Figure 6:
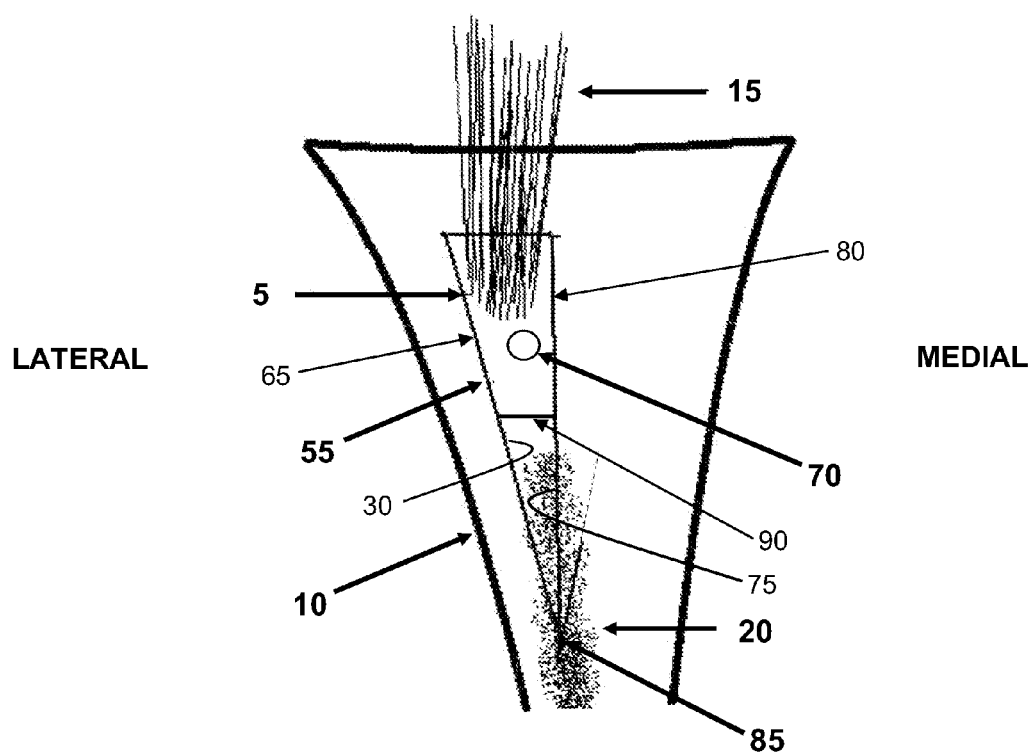
Figure 7:
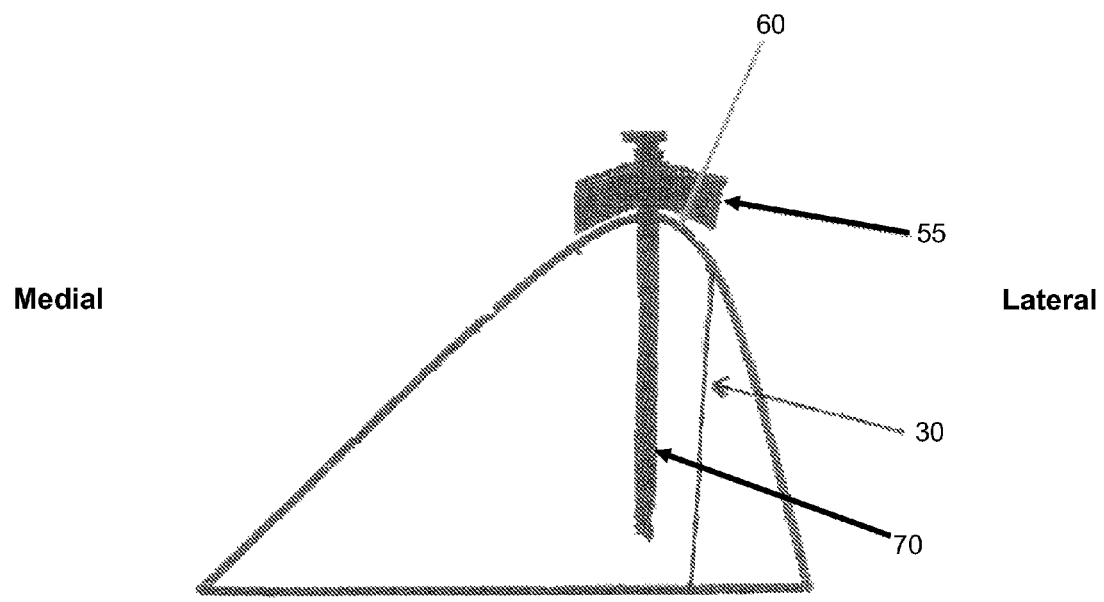
Figure 8:
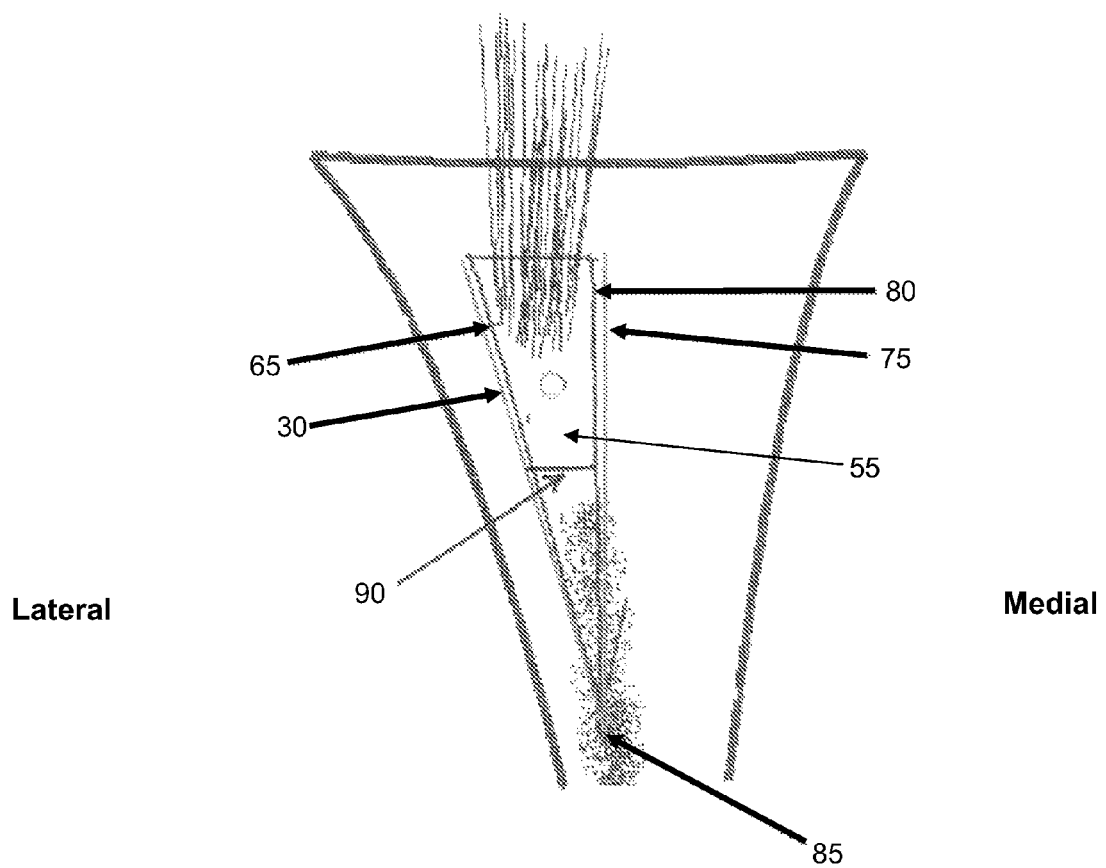

Next, and looking now at FIGS. 6 and 7, an appropriately-sized jig 55 is selected to fit onto tibial tubercle 5. Jig 55 is selected so as to be sized proportional to the size of the portion of the tibial tubercle which is to be transferred. To this end, the surgeon is preferably provided with a surgical kit comprising a plurality of various-sized jigs 55 for use with the tibial tubercle transfer procedure of the present invention. This allows the surgeon to select the appropriate jig 55 for use in a particular patient's procedure. Jig 55 is placed onto the anterior surface 60 of tibial tubercle 5, its lateral edge 65 is aligned with first saw cut 30, and the jig 55 is fixed in place with one or more bone screws 70. Then the body of jig 55 is used to guide a saw cut 75 on the medial side 80 of jig 55, with the body of the jig being configured so that (i) the saw cuts 30, 75 taper to a point distally, and (ii) the saw cuts taper posteriorly.

Figure 9:
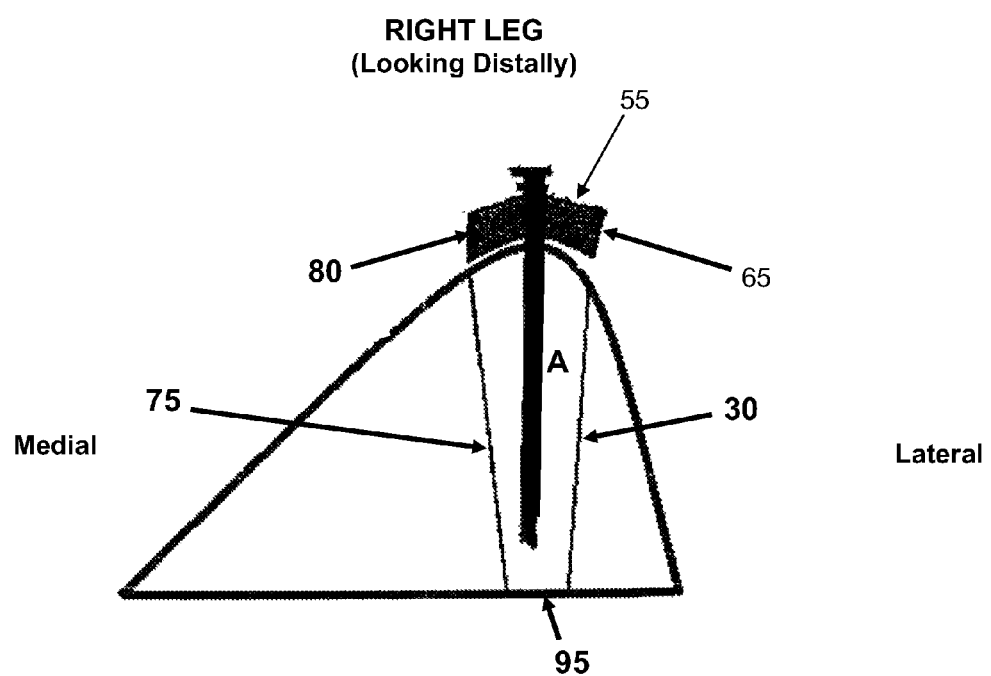

More particularly, and looking now at FIGS. 6-9, surface 80 on the medial side of jig 55 is used to guide saw cut 75 into tibia 10. Note how saw cuts 30 and 75 simultaneously converge toward one another as they extend (i) distally down tibia 10 (FIG. 8), meeting at a point 85 beyond the distal end 90 of jig 55, and (ii) posteriorly into tibia 10 (FIG. 9). Saw cuts 30 and 75 are then completed to the posterior cortex using thin non-tapered osteotomes of the sort known in the art (not shown). The degree of convergence of saw cuts 30 and 75, in the anterior-posterior sense, is such that the two saw cuts 30, 75 may or may not meet before they encounter the posterior cortex, depending upon the size of the patient's tibia, e.g., a face 95 (FIG. 9) of bone may be demarcated between saw cuts 30 and 75 where they open on the posterior cortex.

It should be noted that the degree of displacement of saw cut 75 from saw cut 30 is directly proportional to the amount of the tibial tubercle which is to be transferred during the procedure.

Figure 10:
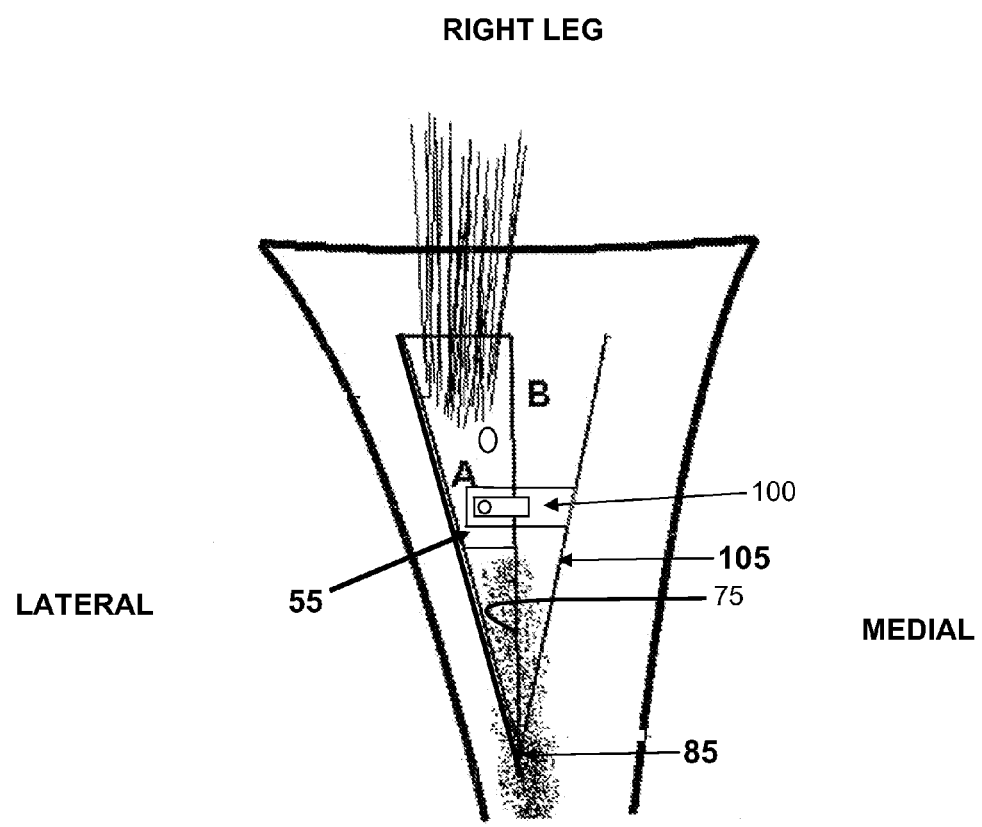
Figure 11:
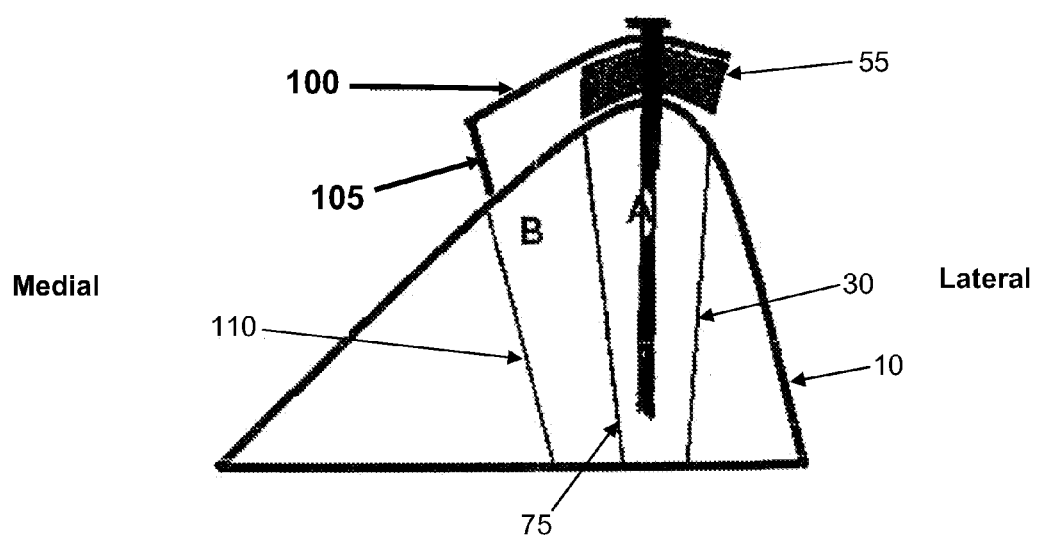
Figure 12:
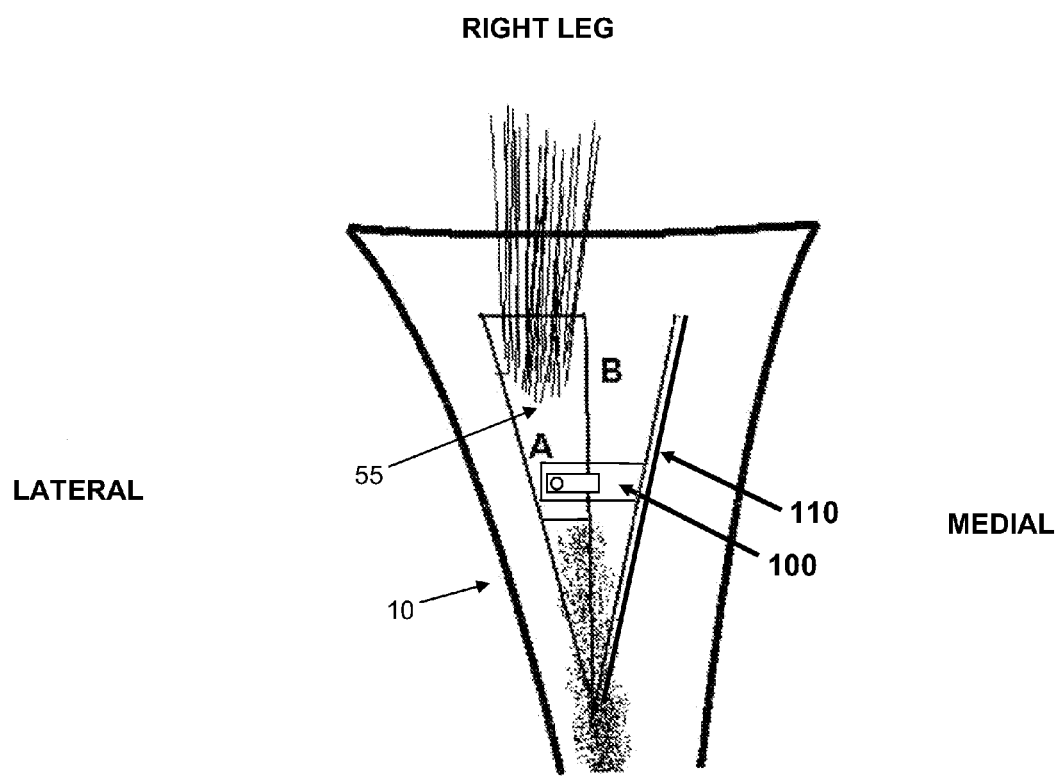
Figure 13:
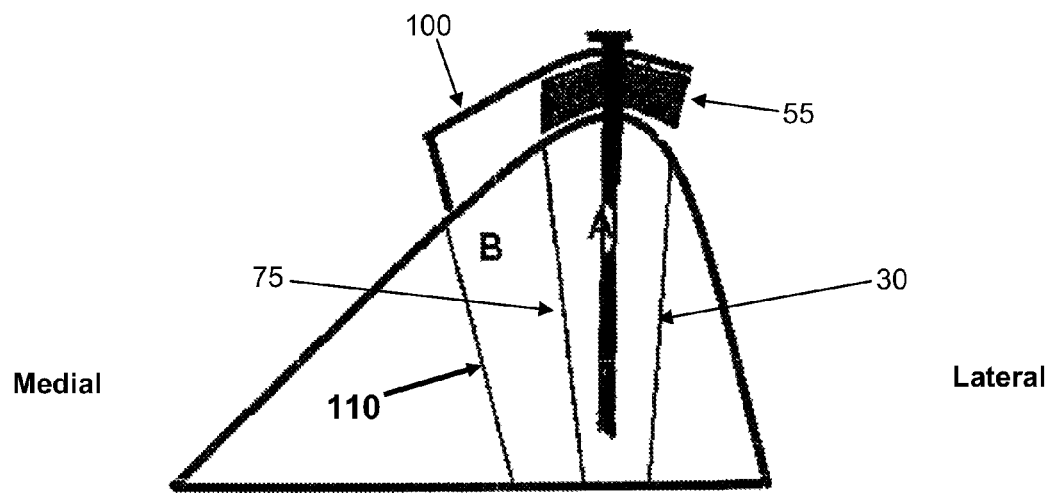

Next, and looking now at FIGS. 10 and 11, an adjustable sidearm 100 is affixed to jig 55. Adjustable sidearm 100 includes a flat saw guide 105 which is angled distally and posteriorly so that it can be used to establish a third saw cut 110 that will meet the two previous saw cuts 30 and 75 at the aforementioned distal point 85. More particularly, sidearm 100 is adjusted relative to jig 55 so that the sidearm's flat saw guide 105 is set to the precise distance that the tibial tubercle is to be moved medially, and then sidearm 100 is locked in place. Then a third saw cut 110 is made along flat saw guide 105. Due to the disposition of flat saw guide 105, and as seen in FIGS. 12 and 13, (i) third saw cut 110 tapers distally so as to meet the two previous saw cuts 30 and 75 at the distal point 85, and (ii) third saw cut 110 tapers posteriorly into tibia 10. Third saw cut 110 is then completed with non-tapered osteotomes so that it may or may not open on the posterior cortex.

It should be noted that the degree of displacement of saw cut 110 from saw cut 75 is directly proportional to the distance which the tibial tubercle is to be moved during the procedure.

Figure 14:
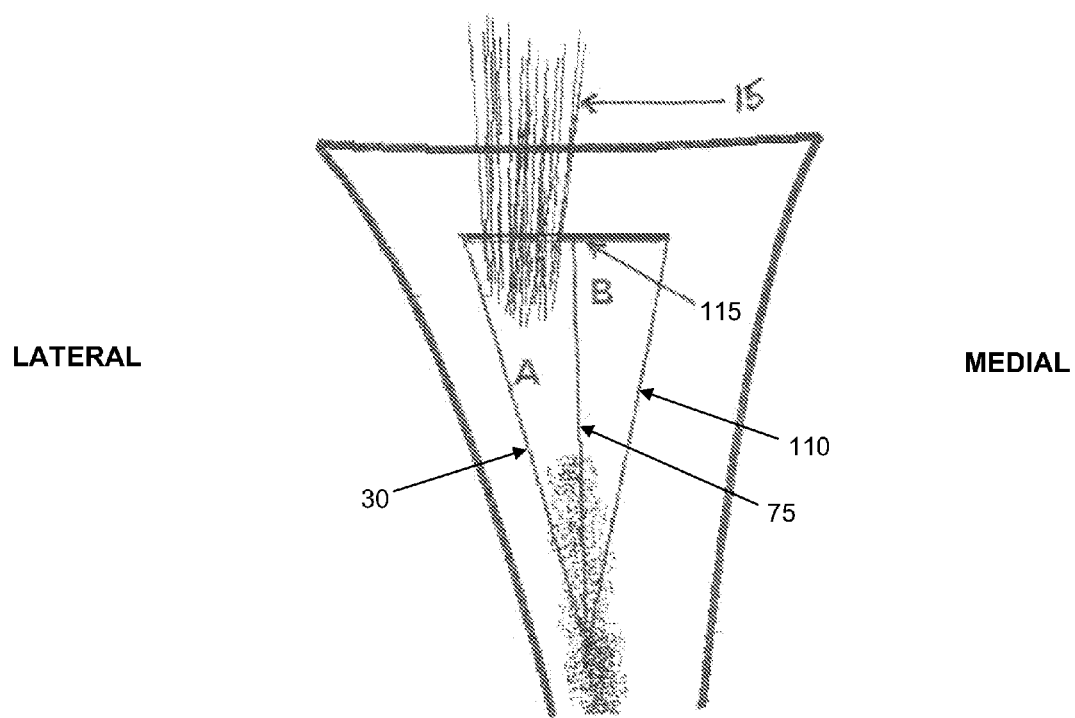

Next, as shown in FIG. 14, a fourth transverse proximal cut 115 is made medially and laterally, perpendicular to the long axis of the tibia, thus creating a first wedge of bone A and a second wedge of bone B. This fourth transverse cut 115 is preferably made with narrow, thin non-tapered osteotomes (not shown) under or subjacent to the patellar tendon 15, which is carefully retracted out of the way so as to avoid injury to the tissue. In this way the two bone blocks A and B are released from the tibia. Then the adjustable sidearm 100 is removed from jig 55.

Figure 15:
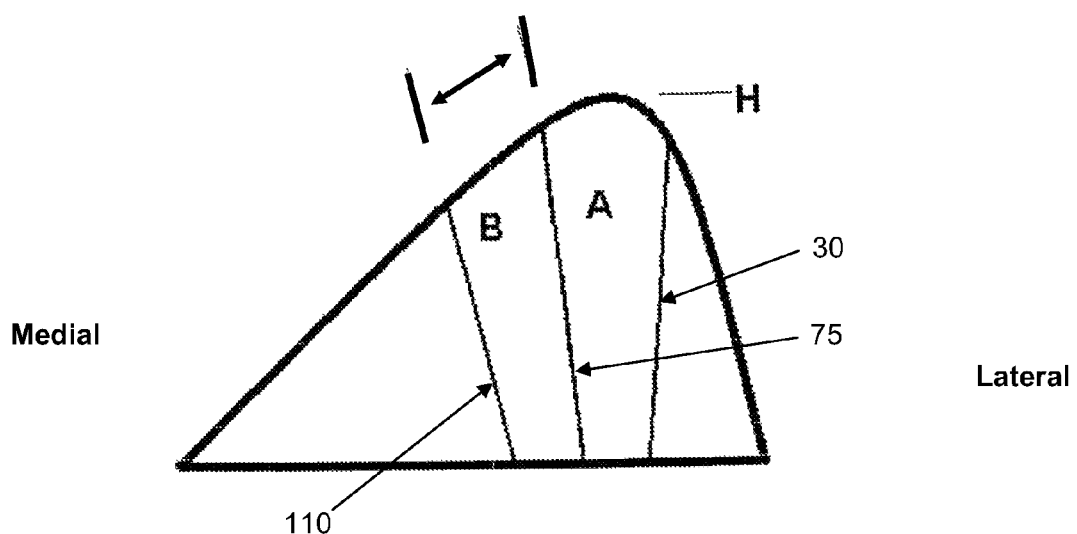
Figure 16:
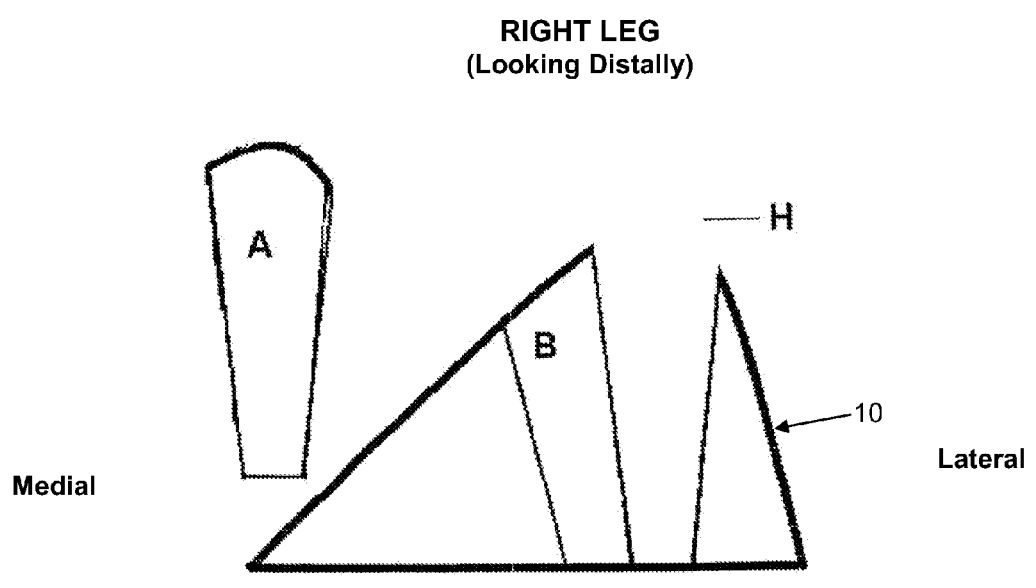
Figure 17:
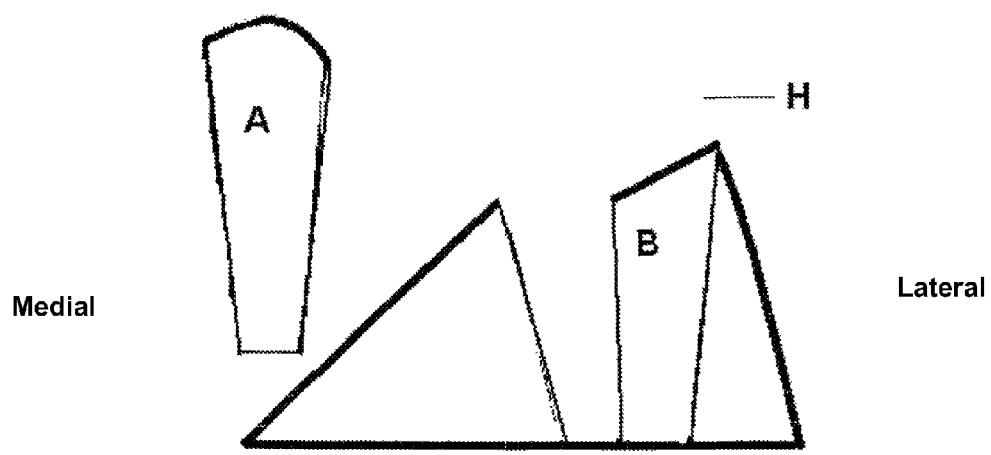

Thus, at this point in the procedure, two somewhat doubly-wedge-shaped (i.e., in a proximal-to-distal sense and in an anterior-to-posterior sense) blocks of bone A and B (FIGS. 14 and 15) have been created, with bone block A having patellar tendon 15 attached to it, and with bone block B sitting medial to bone block A.

By exchanging the side-by-side positioning of bone blocks A and B, the tibial tubercle (and patellar tendon) may be transferred medially.

Figure 18:
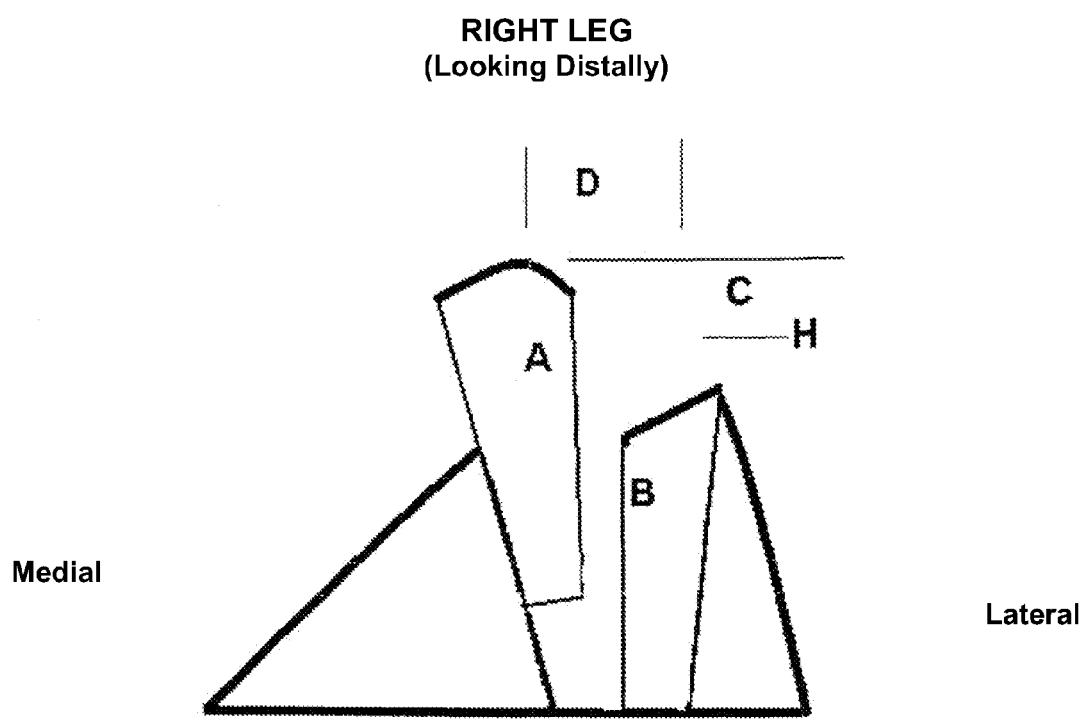
Figure 19:
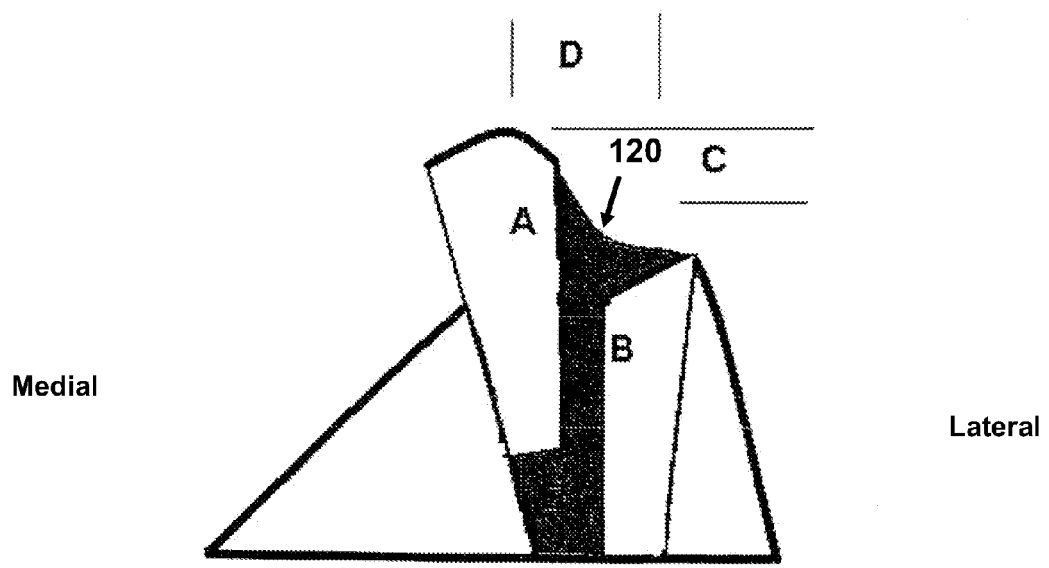

More particularly, and looking now at FIGS. 16-22, the positions of the wedge-shaped bone blocks A and B are exchanged by (i) removing bone block A from tibia 10 (FIG. 16), (ii) transferring bone block B laterally (FIG. 17), and (iii) inserting bone block A back into tibia 10, medially of bone block B (FIG. 18). Alternatively, bone block B can be removed from the tibia, bone block A shifted laterally, and then bone block B inserted back into the tibia, medially of bone block A.

To achieve a tight fit, and to compensate for the bone lost in the saw kerfs, bone graft material 120 (FIG. 19) can be inserted into tibia 10, medially and laterally of, and between, bone blocks A and B.

Furthermore, as bone block A is inserted back into tibia 10, the anterior-posterior position of bone block A may be adjusted. More particularly, if anterior transfer of the tibial tubercle is desired, additional bone graft material can be inserted posterior to the transferred tibial tubercle bone block, thereby anteriorly advancing the tibial tubercle bone block the desired distance.

Figure 20:
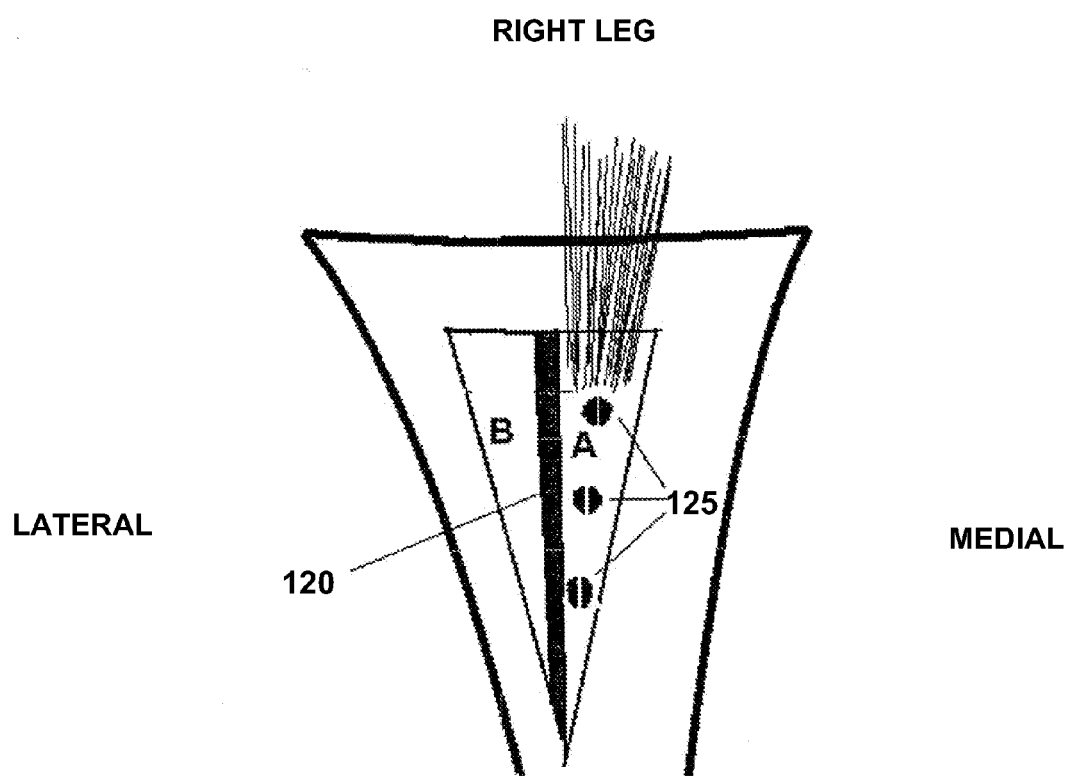
Figure 21:
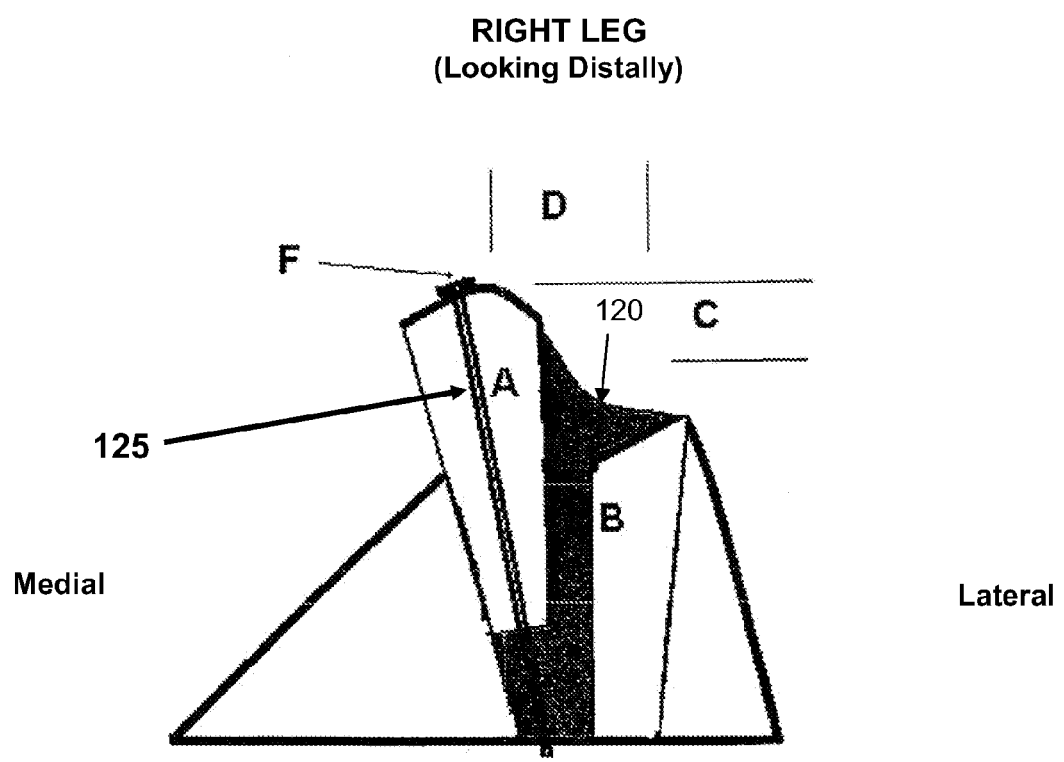
Figure 22:
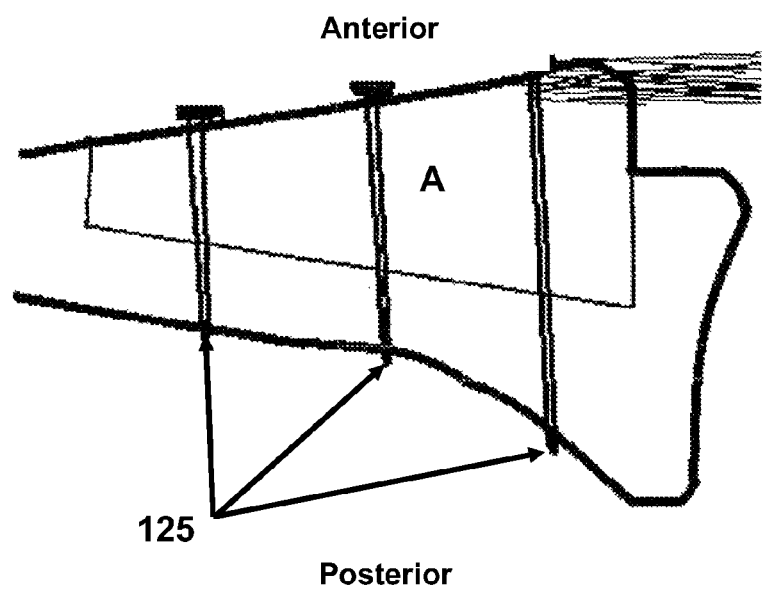
Figure 23:
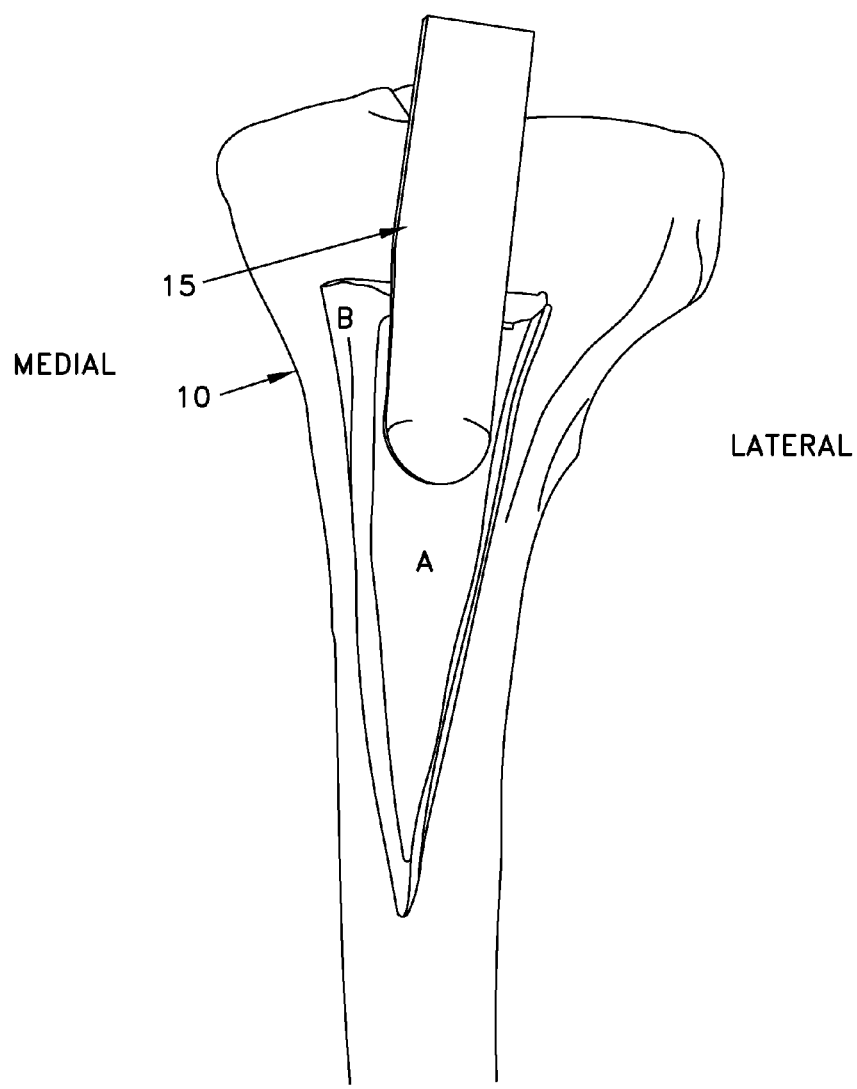
FIGS. 23-27 are a series of photographs showing the tibial tubercle transfer procedure being effected on "saw bones"
Figure 24:
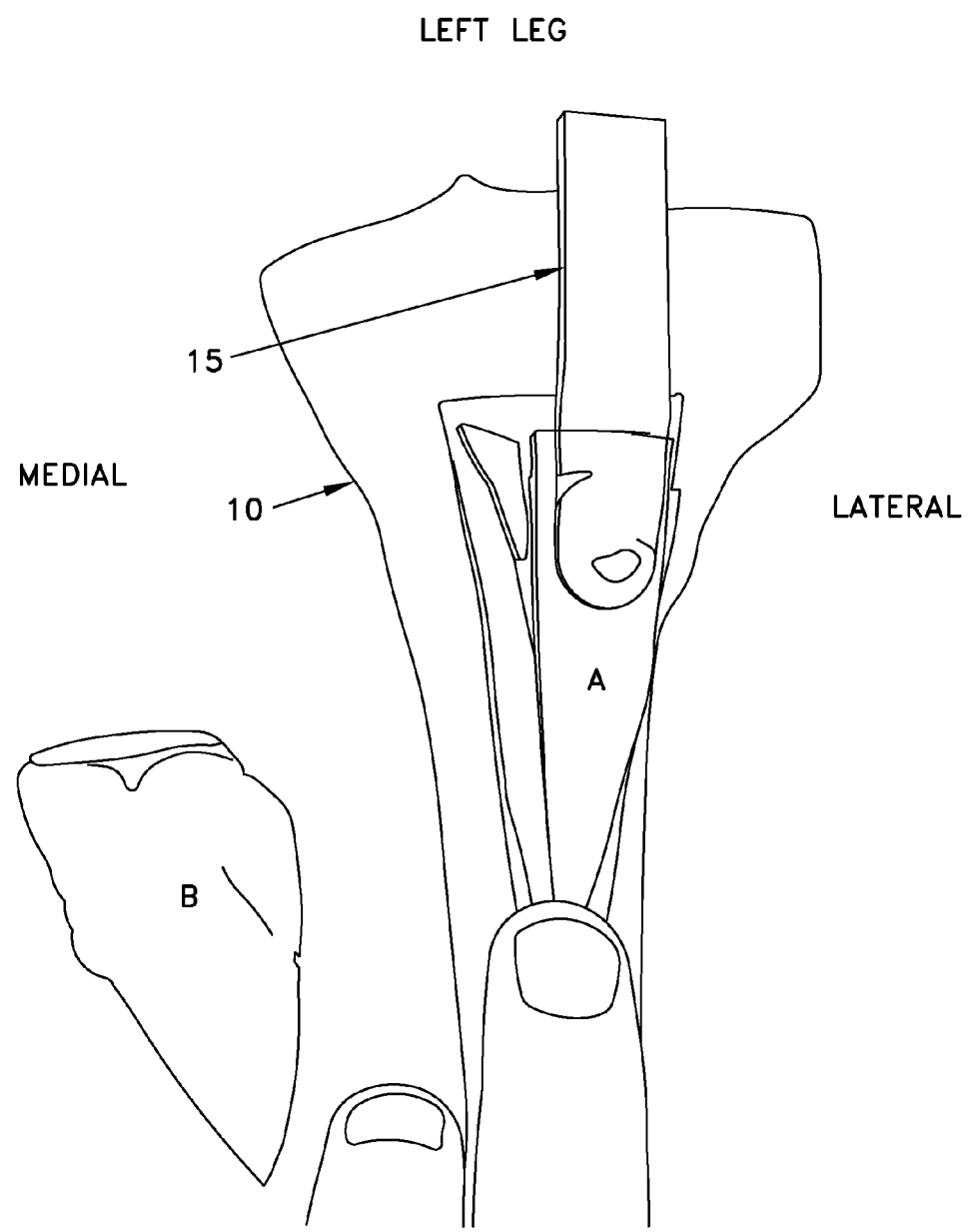
Figure 25:
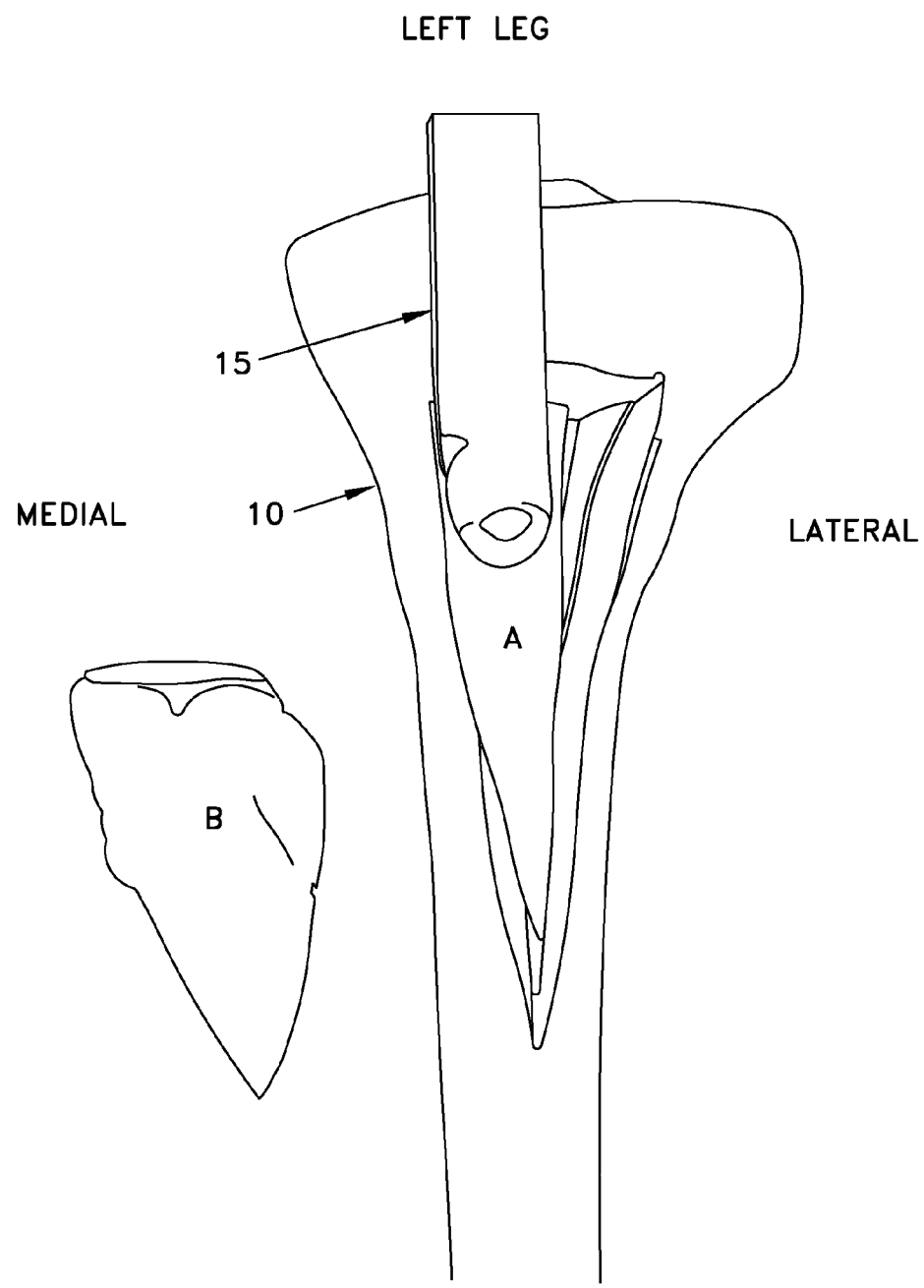
Figure 26:
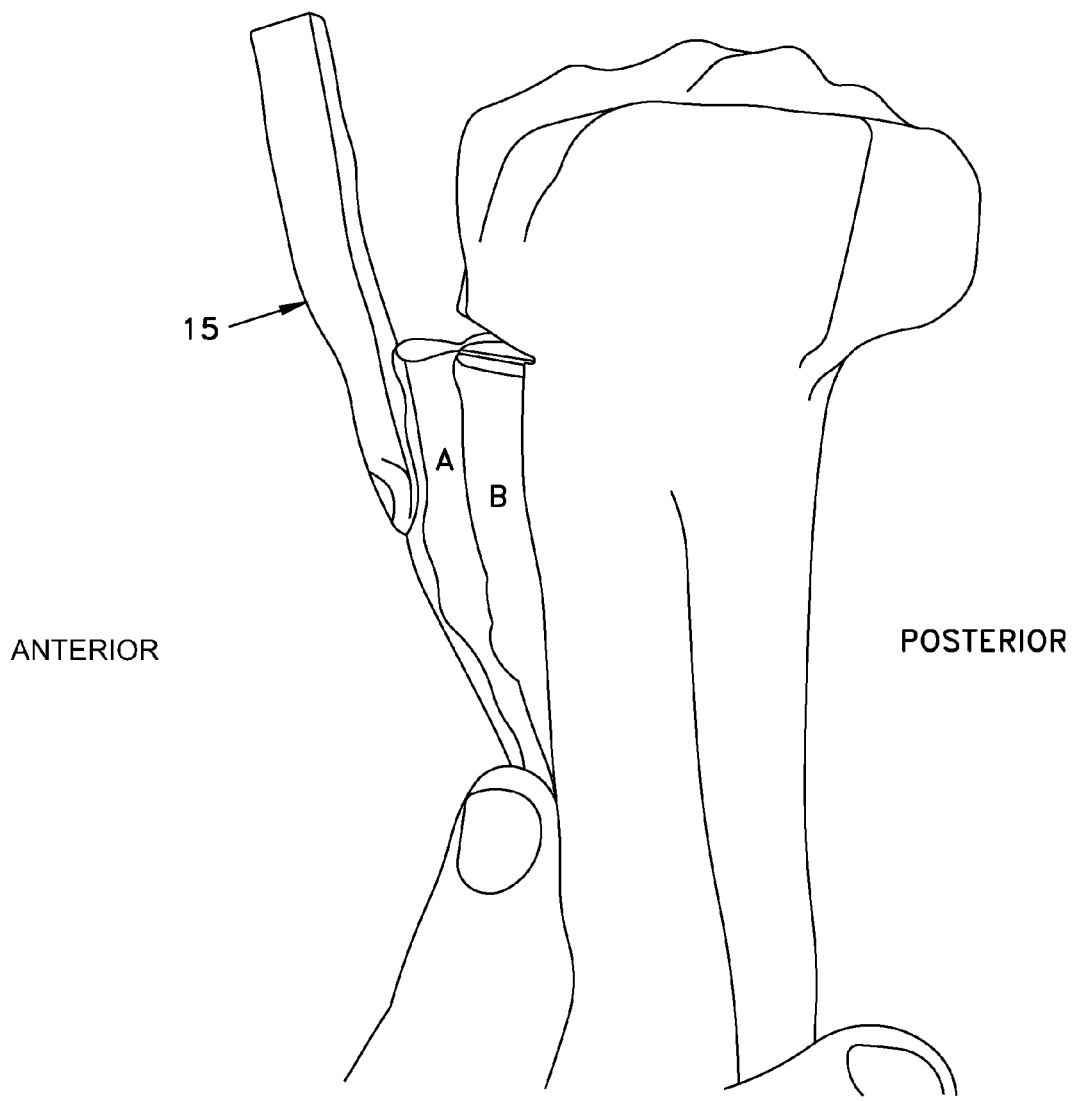
Figure 27:
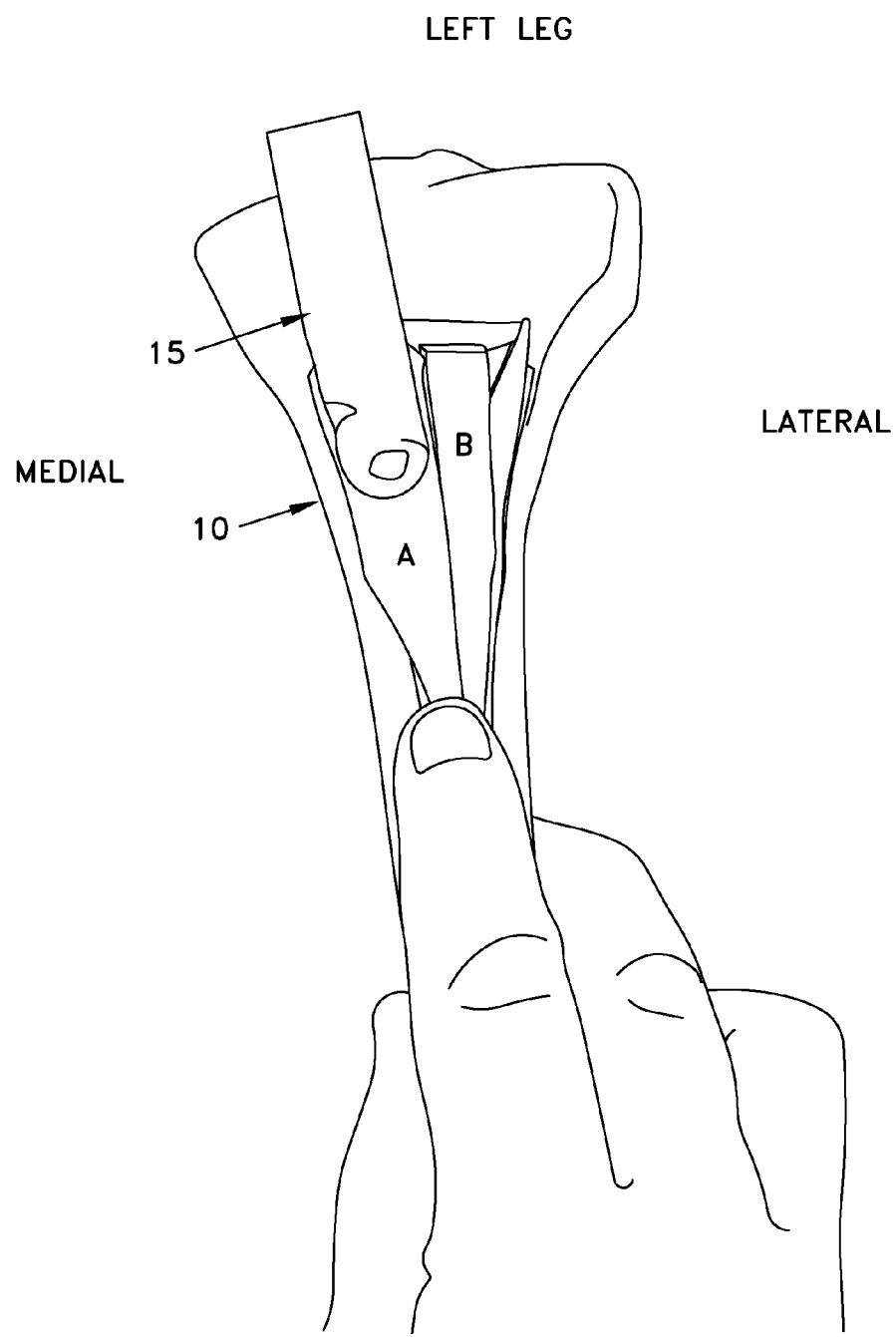

Finally, the transferred tibial tubercle is fixed in its new position using multiple bone screws, e.g., bone blocks A and B are secured in position using a plurality of bone screws 125 (FIGS. 20-22). If desired, the screw holes on the anterior surface of the bone may be countersunk so as to prevent the screw head from irritating soft tissues. Alternatively, and/or additionally, the transferred tibial tubercle may be fixed in its new position using bone cement and/or bone adhesive, to the extent that such cement and/or adhesive is available.

See also FIGS. 23-27, which are a series of photographs showing the tibial tubercle transfer procedure being conducted on "saw bones".

Among other things, by adjusting the positioning of jig 55 and fourth transverse cut 115, distally or proximally, transfer of the tibial tubercle distally or proximally on the tibia can be achieved as well.

Furthermore, adjustable sidearm 100 is preferably designed to be attached to either side of jig 55 so as to accommodate right or left knees. This approach also allows the device to be used for the relatively rare lateral tibial tubercle transfer, e.g., when revising an over-medialized previous tibial tubercle transfer.

Shim Construction

In another form of the present invention, the aforementioned jig 55 is replaced by a base jig (see below), and the aforementioned sidearm 110 is replaced by a shim (see below), wherein the shim mounts to the base jig with a tongue-and-groove construction or other construction, as will hereinafter be discussed.

In this form of the invention, the tibial tubercle transfer is preferably effected as follows.

Step 1. Make a longitudinal skin incision slightly lateral of midline, just lateral to the patellar tendon and tibial crest.

Step 2. Dissect/release the subcutaneous tissues as required.

Step 3. Dissect the retro-patellar tendon space between the patellar tendon insertion (into the tibial tubercle) and the patella.

Step 4. As seen in FIGS. 3-5, an end-cutting oscillating bone saw (not shown) comprising a saw blade 25 is used to make a short plunge-cut 30 at the lateral edge of tibial tubercle 5, directed posteromedially to avoid cutting the lateral tibial cortex and aligned to meet anterior tibial crest 20 of tibia 10 at a point distal to tibial tubercle 5. Saw blade 25 is detached from the bone saw, leaving the saw blade in the cut 30. The distal end 35 of lateral saw guide 40 is positioned over tibial crest 20, the lateral saw guide bar is brought up against saw blade 25, and the proximal end 45 of lateral saw guide 40 is secured to tibia 10, e.g., with a fixation pin 50. With lateral saw guide 40 thus fixed to the proximal tibia 10, saw blade 25 is removed from the bone and re-attached to the bone saw, whereupon the first cut 30 is completed.

Figure 28:
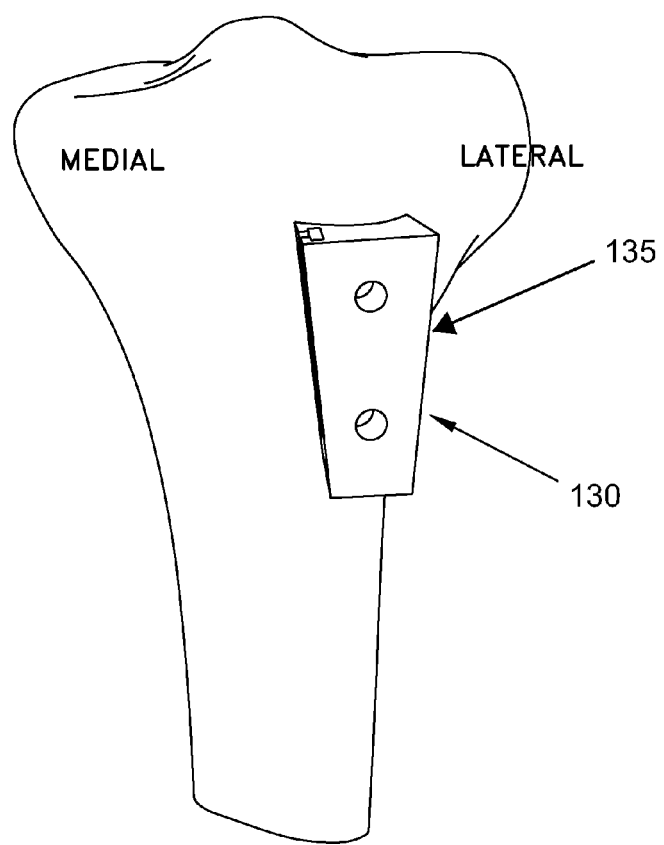
FIGS. 28-45 are a series of schematic views showing the novel tibial tubercle transfer procedure of the present invention being effected using another novel form of apparatus.

Step 5. Position the base jig 130 (FIG. 28) on the tibial tubercle, with the lateral side 135 of the base jig aligned with the first (lateral) cut 30. Base jig 130 is selected so as to be sized proportional to the size of the portion of the tibial tubercle that is to be transferred. To this end, the surgeon is preferably provided with a surgical kit comprising a plurality of various-sized base jigs 130 for use with the tibial tubercle transfer procedure of the present invention. This allows the surgeon to select the appropriate size base jig for use in a particular patient's procedure.

Figure 29:
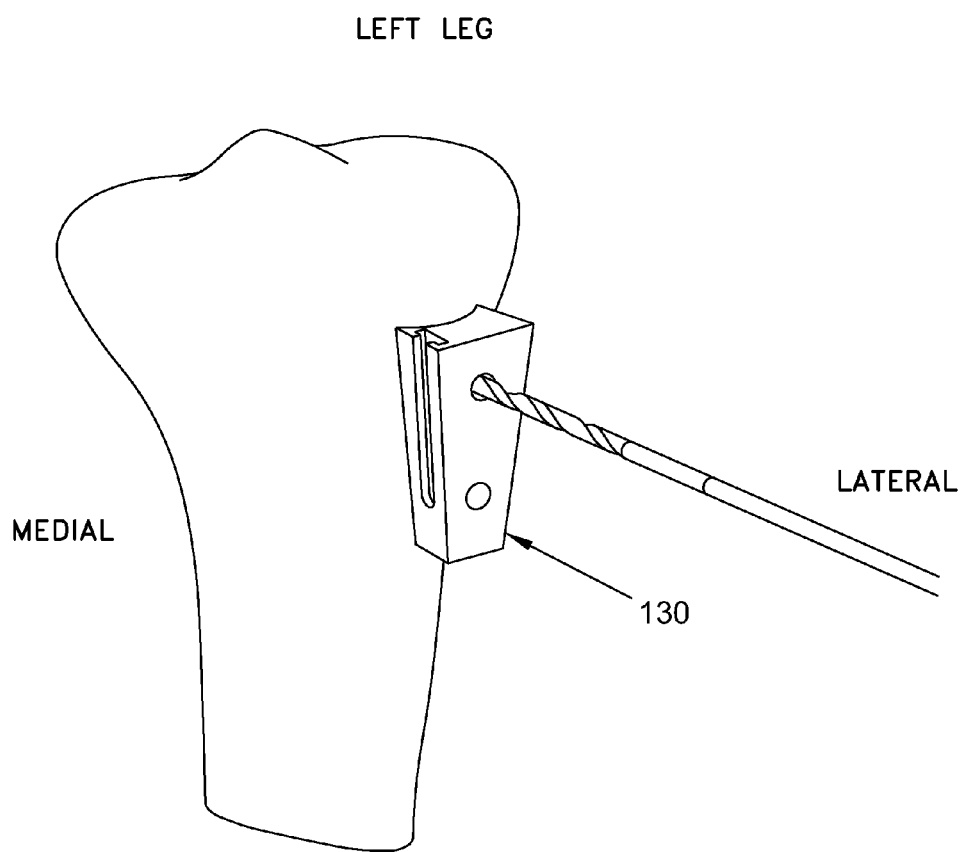
Figure 30:
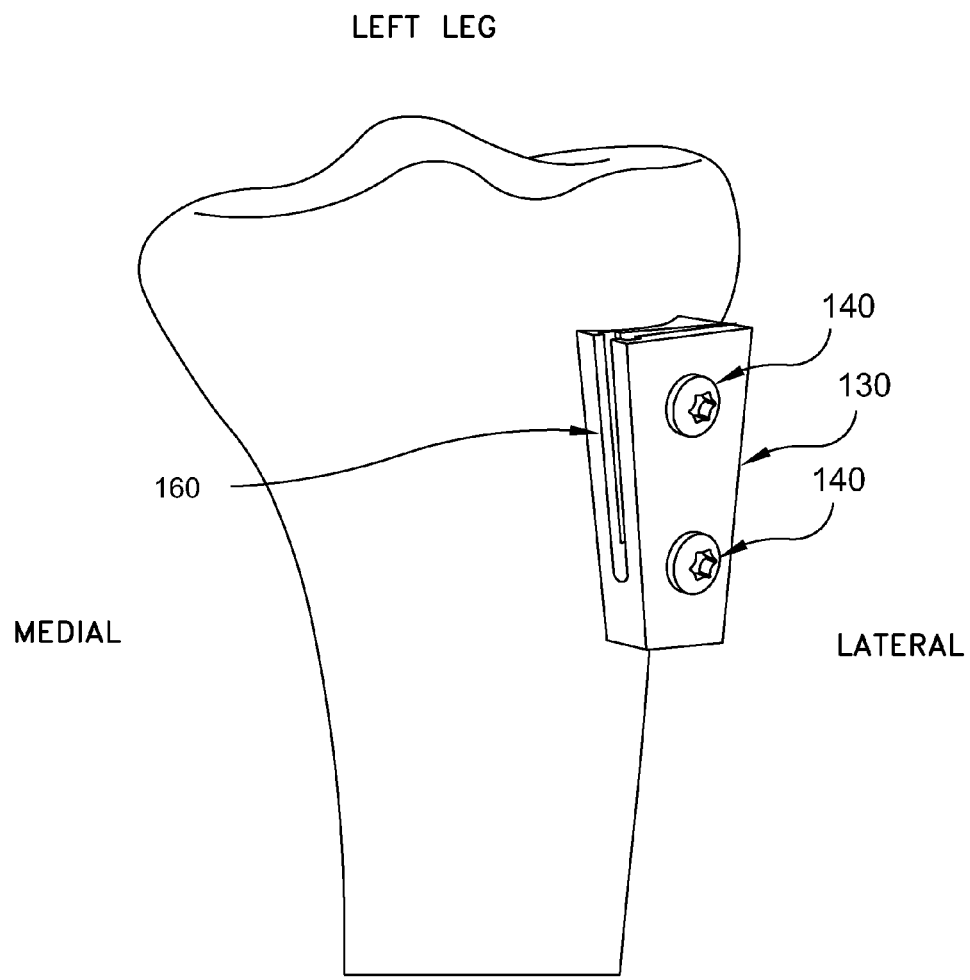
Figure 31:
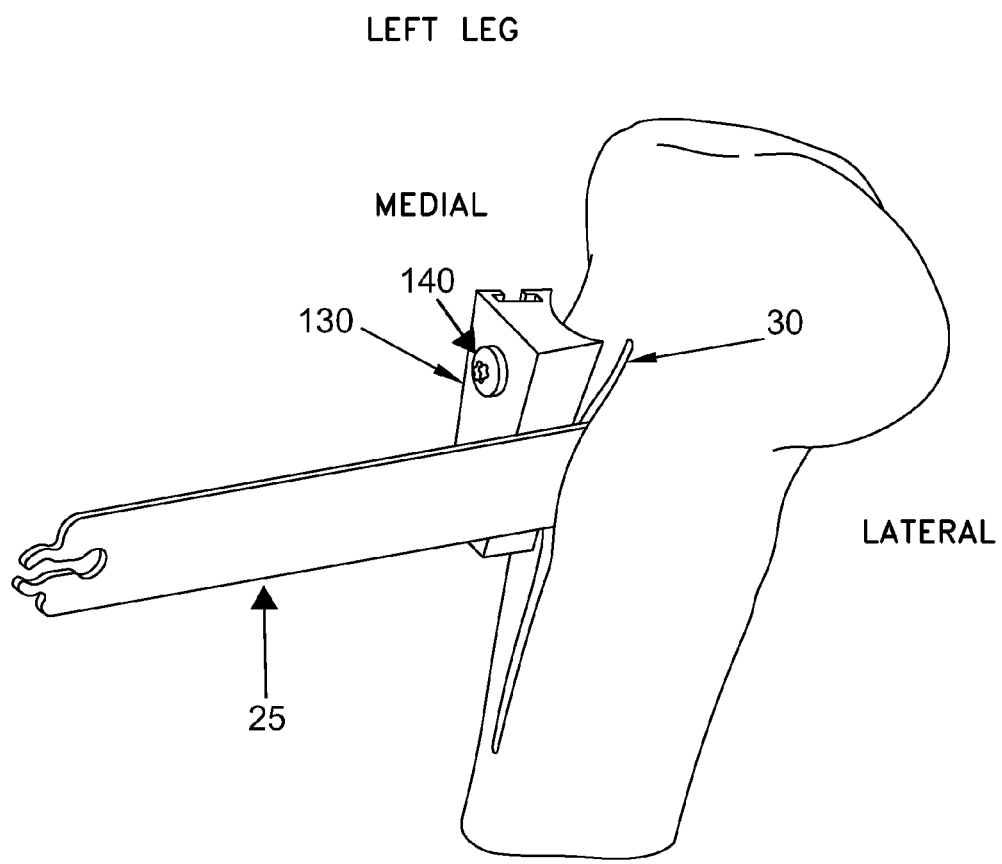

Step 6. Drill pilot holes through base jig 130 (FIG. 29) and fix base jig 130 to tibial tubercle 5 using appropriately-sized bone screws 140 (FIG. 30). If desired, saw blade 25 may be left in first (lateral) cut 30 while this is done so as to help stabilize base jig 130 relative to tibia 10 (FIG. 31).

Figure 32:
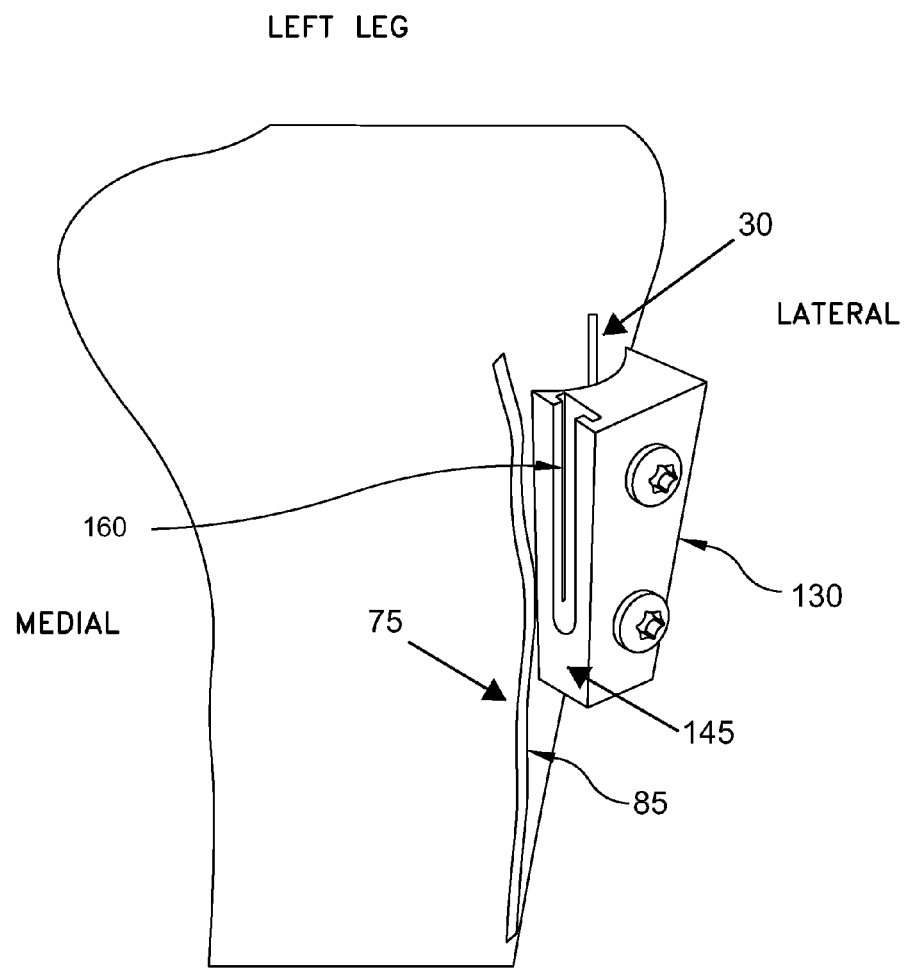

Step 7. Holding a saw blade flush against the medial face 145 of base jig 130, make the medial longitudinal cut 75 through the cortical bone, extending the cut inferiorly beneath the skin until the two cuts 30 and 75 intersect at point 85 (FIG. 32).

Figure 33:
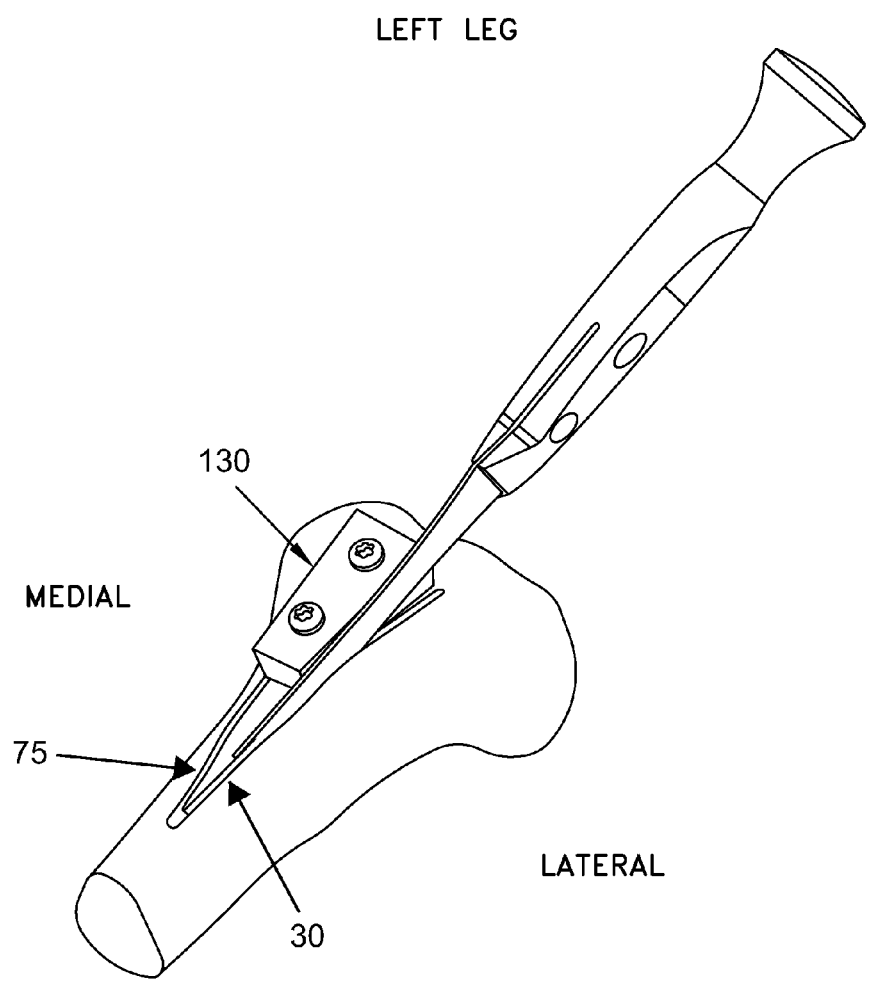

Step 8. Using a thin non-tapered osteotome, deepen the cuts to the posterior cortex (FIG. 33) to complete bone block A.

Figure 34:
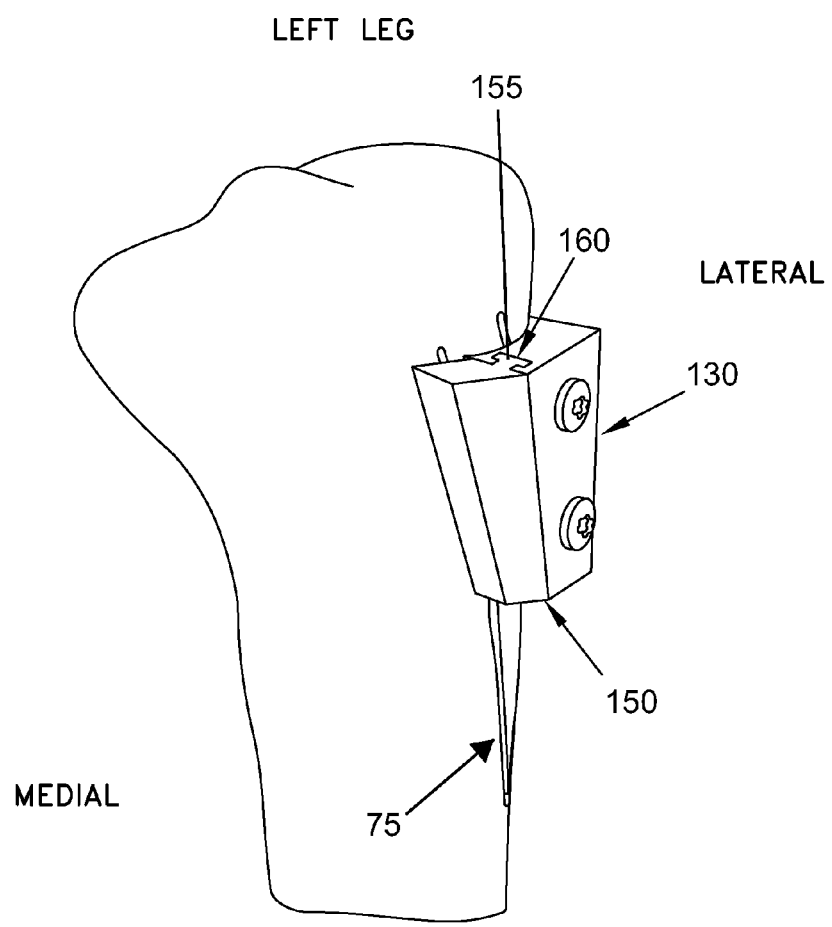

Step 9. Attach the shim 150 to base jig 130 (FIG. 34). In one preferred form of the invention, this is done by inserting a tongue 155 of shim 150 into a groove 160 of base jig 130. Alternatively, shim 150 may be provided with the groove 160, and base jig 130 may be provided with the tongue 155. Furthermore, it should also be appreciated that shim 150 may be fixed to base jig 130 using other means, e.g., by screwing, by press-fitting, etc. Shim 150 is sized in accordance with the desired medialization or lateralization increment. To this end, the surgeon is preferably provided with a surgical kit comprising a plurality of various-sized shims for use with the tibial tubercle transfer procedure of the present invention. This allows the surgeon to select the appropriate shim for use in a particular patient's procedure.

Figure 35:
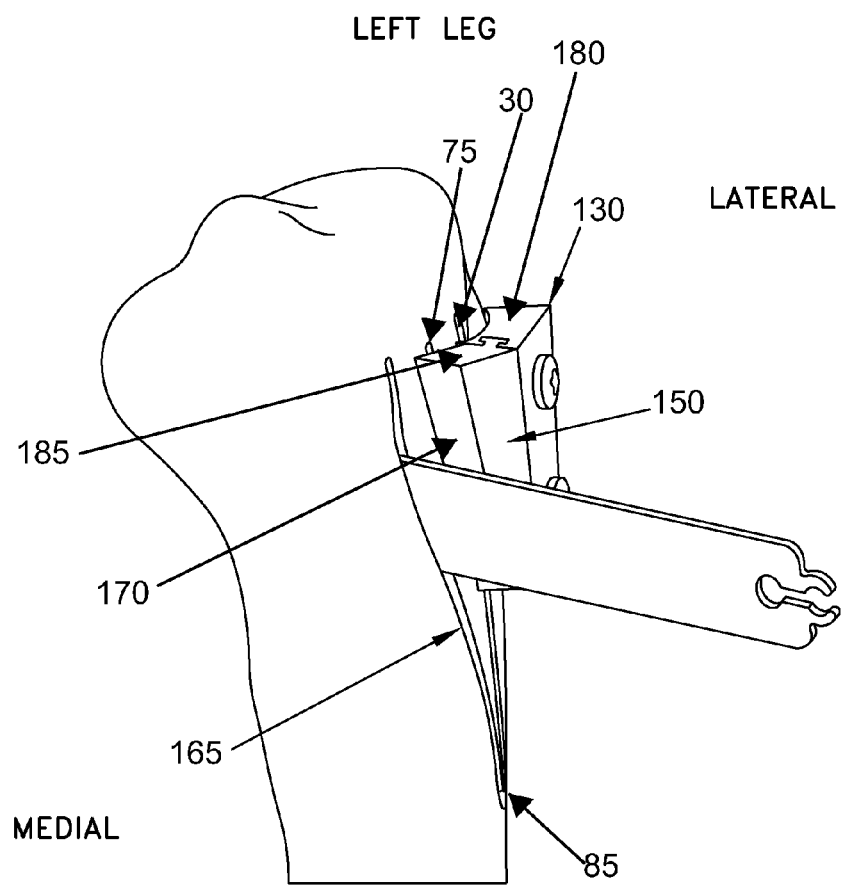

Step 10. Create bone block B by making a third longitudinal cut 165 along the medial side 170 of shim 150, using the saw and osteotomes as in Steps 7 and 8, intersecting the previous two cuts 75, 30 inferiorly at their apex at point 85 (FIG. 35).

Figure 36:
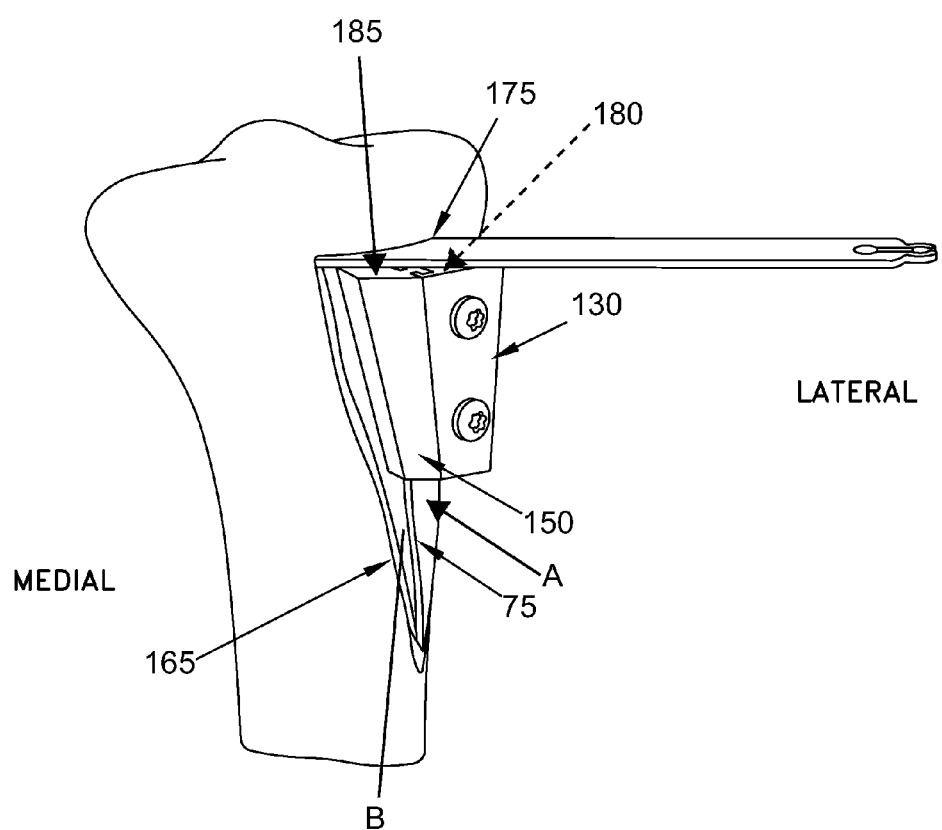

Step 11. Make a transverse cut 175, posterior to the patellar tendon, which is carefully retracted out of harm's way, using the superior faces 180, 185 of base jig 130 and shim 150, respectively, as a reference to complete the two wedges forming bone blocks A and B (FIG. 36).

Figure 37:
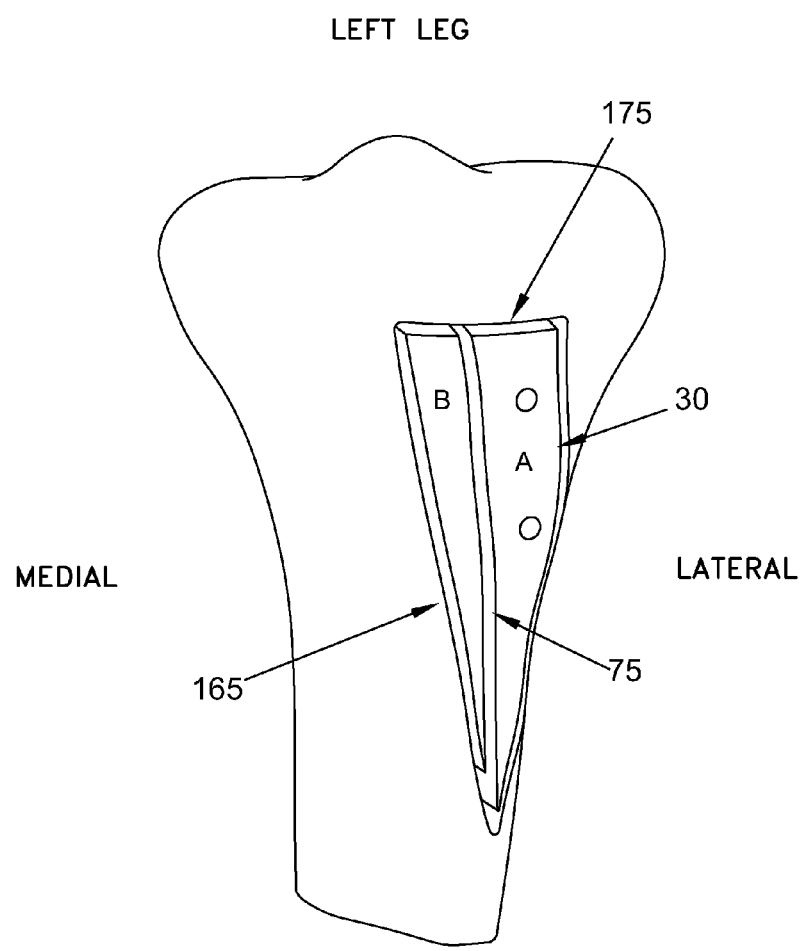
Figure 38:
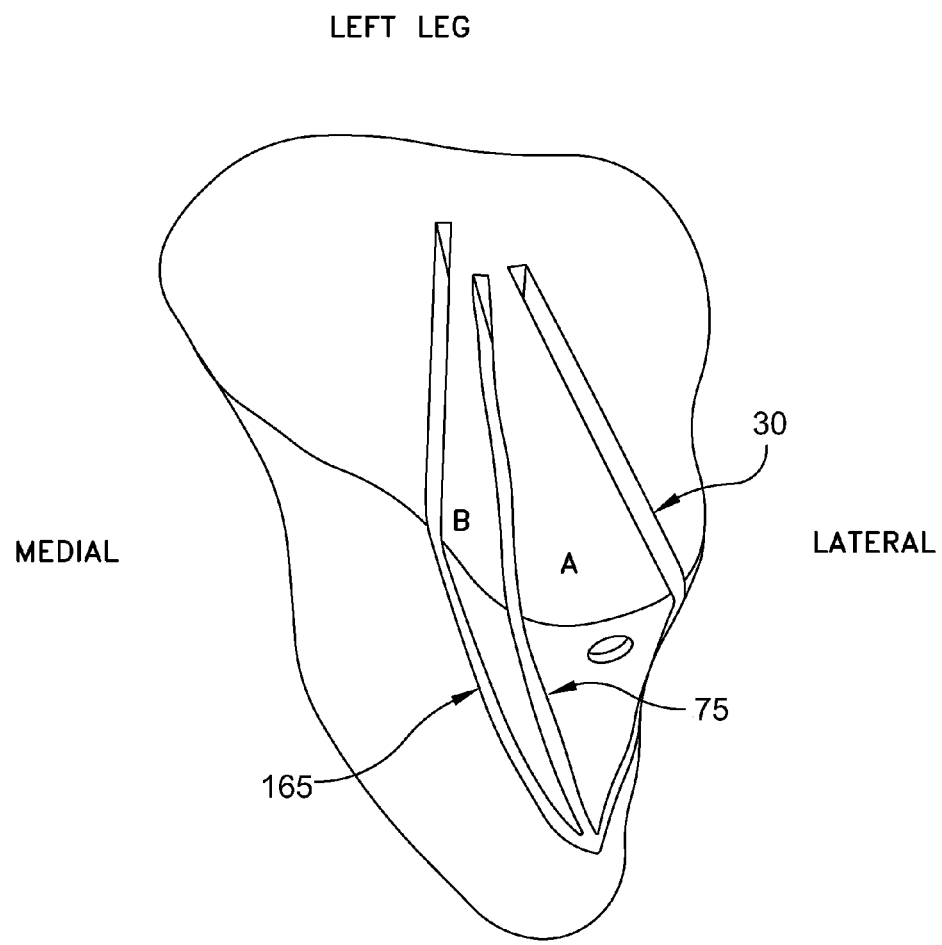

Step 12. Remove shim 150 from base jig 130. Base jig 130 may be removed from tibia 10 at this point or, more preferably, it may remain attached to bone block A so as to facilitate manipulation of the bone block and for use in subsequent steps (see below). FIGS. 37 and 38 show frontal and section views of the tibia after the four cuts 30, 75, 165 and 175 have been completed (for clarity of illustration, base jig 130 is shown removed from bone block A in these views).

Step 13. Release the wedges from their attachments by applying appropriate hand or finger force.

Figure 39:
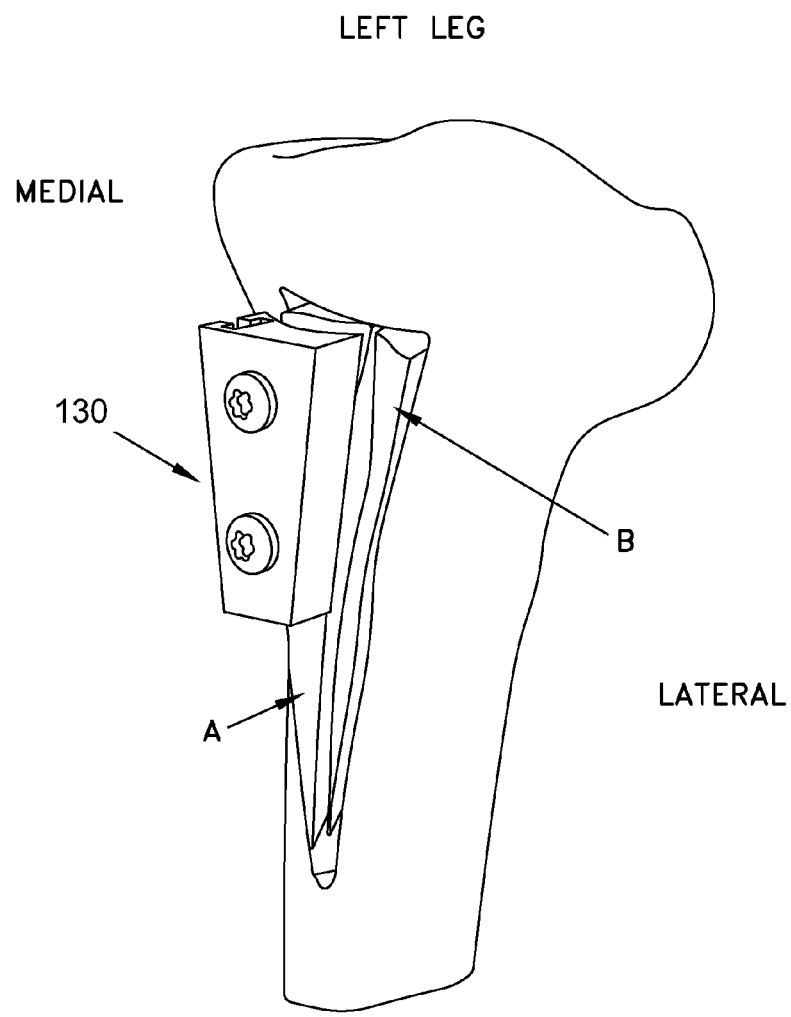

Step 14. Lift out and transpose the cut wedges so as to move the tibial tubercle into the medial position (FIG. 39).

Step 15. Pack bone graft material into the spaces between and around the bone wedges as needed. If anteriorization is desired, pack bone graft material behind bone block A so as to create the correct distance of anterior wedge displacement.

Step 16. Measure the Q-angle intra-operatively to assure the desired correction.

Step 17. Unscrew and remove the distal bone screw 140 from base jig 130.

Figure 40:
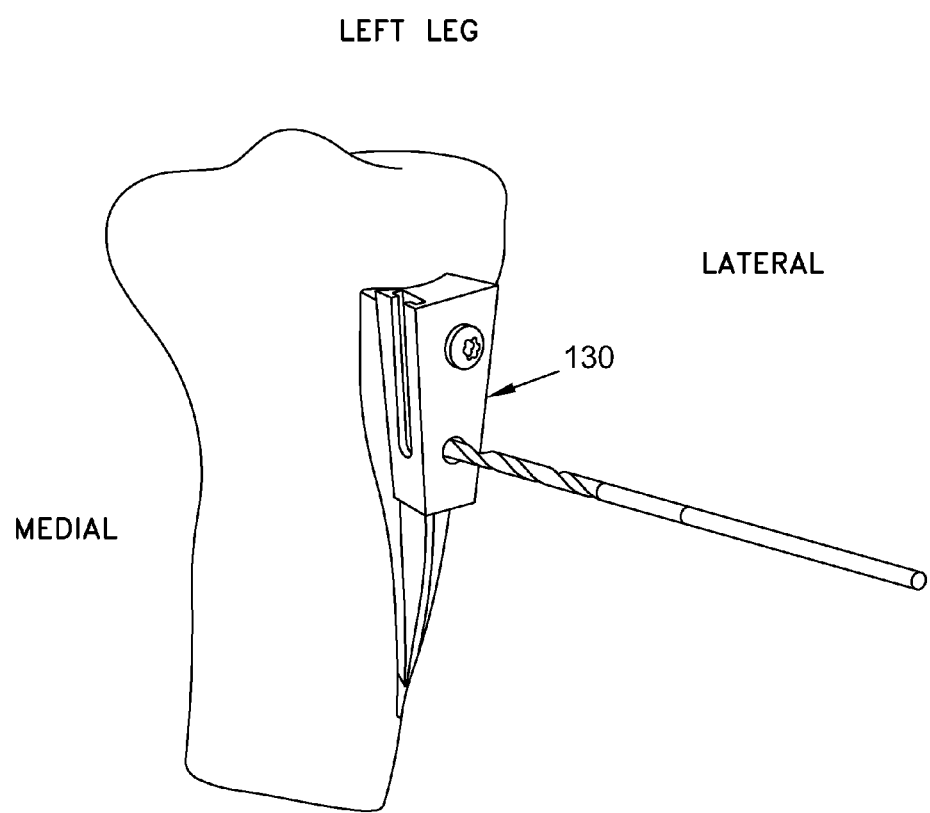

Step 18. Holding tibial tubercle 5 in its new position, drill a pilot hole through the distal hole in base jig 130, through the tibial tubercle bone block A, and through the posterior cortex with the knee flexed, using special care as the drill penetrates the posterior cortex (FIG. 40).

Step 19. Remove proximal bone screw 140 and remove base jig 130.

Step 20. Measure the length of the distal pilot hole and select a fixation screw of sufficient length to just penetrate the posterior cortex.

Figure 41:
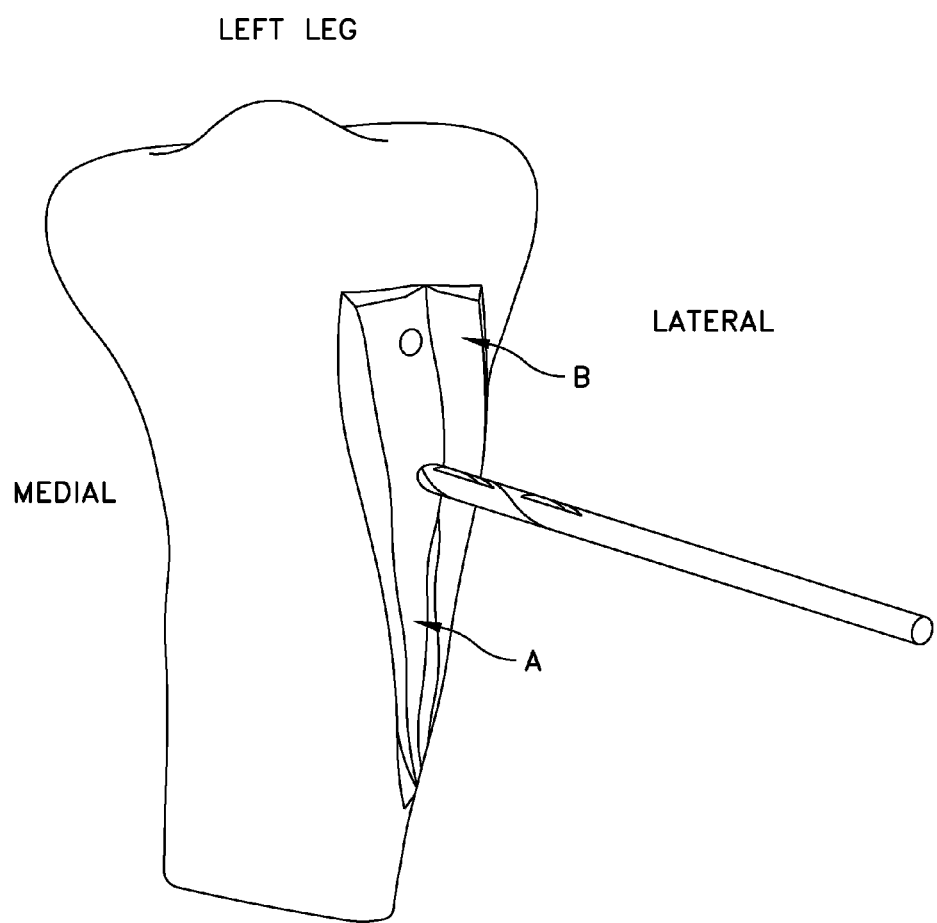

Step 21. Over-drill the distal tibial tubercle pilot hole a short distance with a drill bit of the appropriate size to create a thread lag (FIG. 41).

Figure 42:
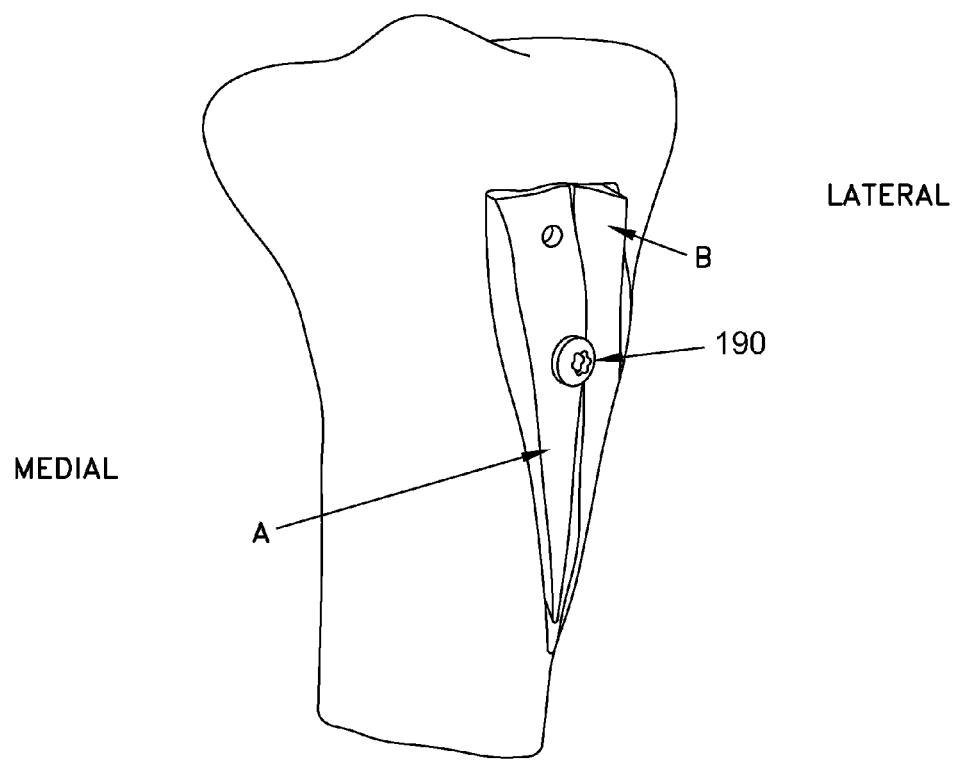

Step 22. Insert and secure the first (distal) fixation screw 190 (FIG. 42).

Figure 43:
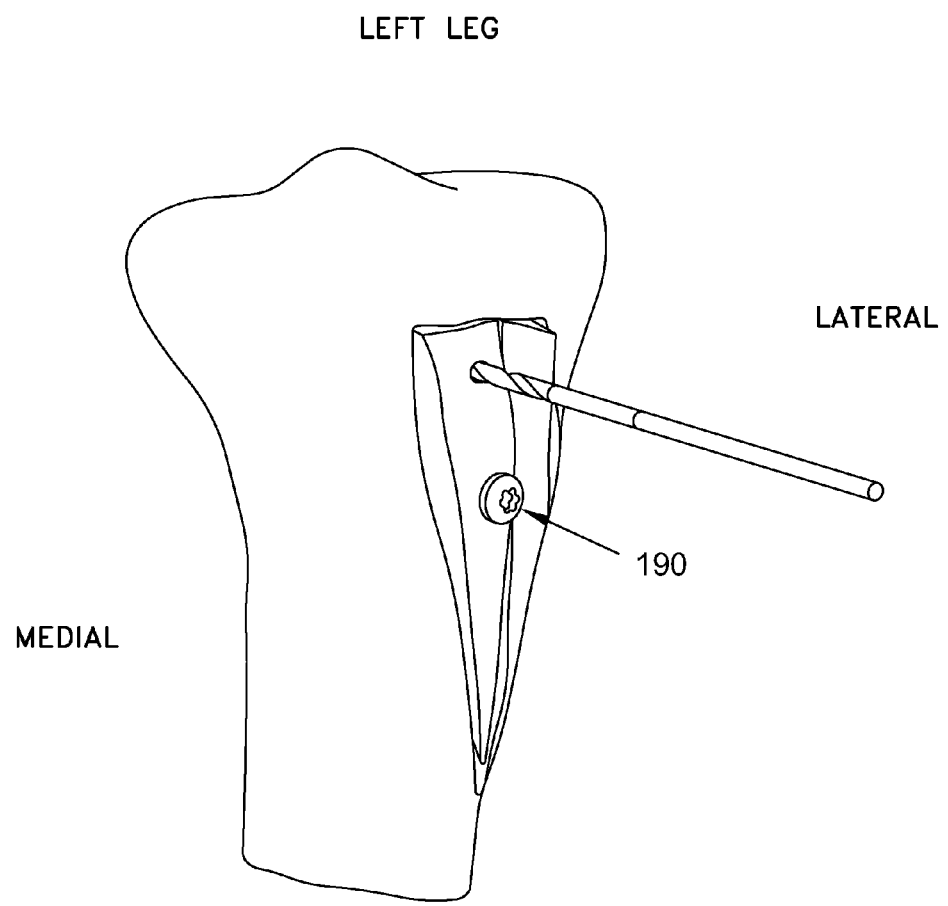
Figure 44:
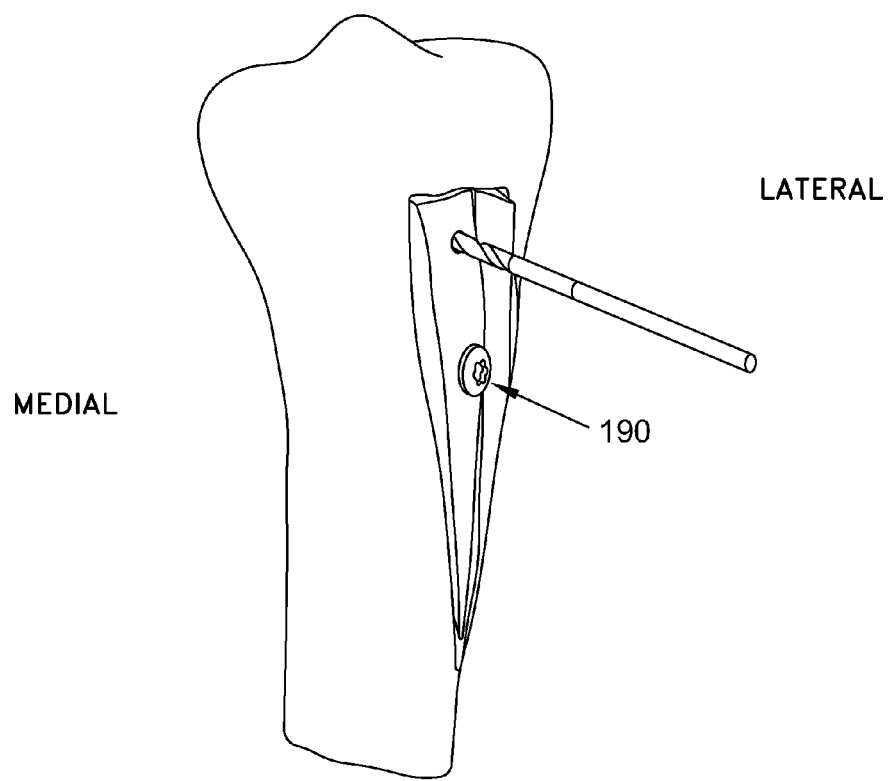
Figure 45:
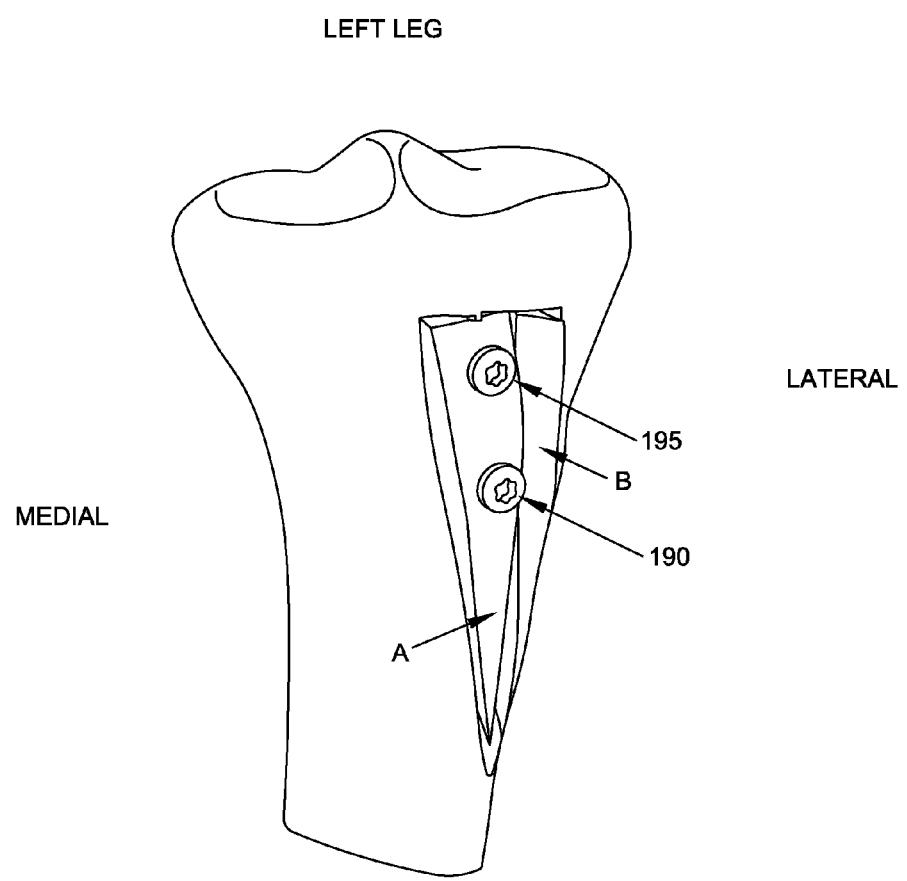

Step 23. Repeat Steps 18-22 for a fixation screw 195 in the proximal hole (FIGS. 43-45).

Step 24. (Optional) If a third fixation screw is desired, drill a pilot hole to and through the posterior cortex carefully as above in the preferred location, over-drill the pilot hole a short distance to create a thread lag, and insert the appropriate length cortical bone screw. All screws will thus provide excellent secure bi-cortical bone fixation with lag effect.

If desired, the screw holes on the anterior surface of the bone may be countersunk so as to prevent the screw head from irritating soft tissues.

Step 25. Alternatively, and/or additionally, the transferred tibial tubercle may be fixed in its new position using bone cement and/or bone adhesive, should such material of sufficient strength be available.

Sidearm With Arcuate Guide

In the foregoing disclosure, there is taught a sidearm construction for effecting the tibial tubercle transfer. Specifically, in the foregoing form of the invention, a jig 55 (having a lateral edge 65 and a cutting surface 80) and a sidearm 100 (having a flat saw guide 105) are used to cut out bone blocks A and B. As seen in FIGS. 10 and 12, sidearm 100 has a substantially linear body including a substantially linear slot. However, inasmuch as flat saw guide 105 must be angled so that it is aimed at distal point 85 (FIG. 8), the sidearm's substantially linear body and substantially linear slot permit relatively limited adjustability for the sidearm. As a result, it is generally necessary to provide a robust set of sidearms, each having different dimensions, in order to accommodate different degrees of offset for the third (medial) saw cut 110.

Figure 46:
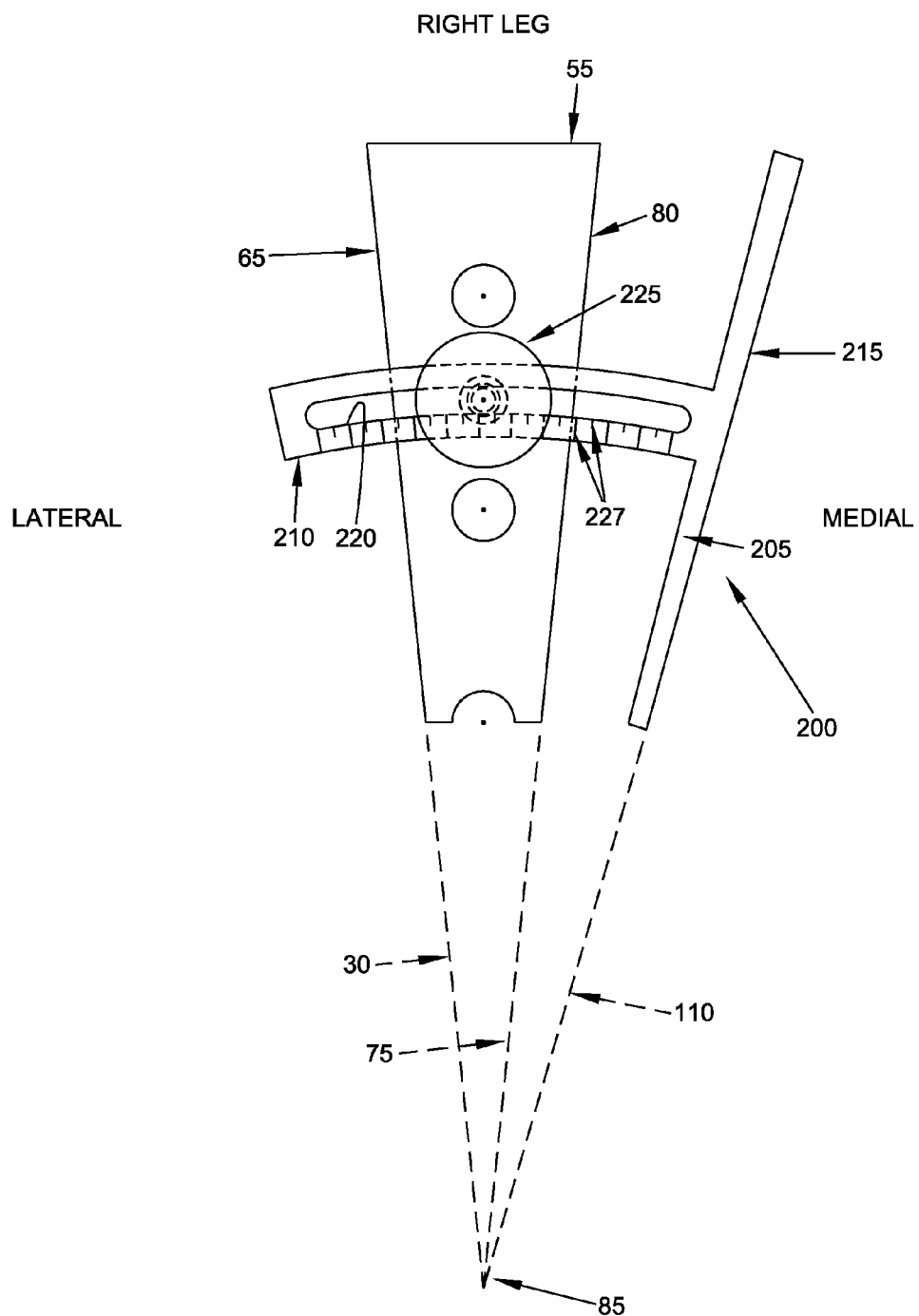
FIGS. 46 and 47 are schematic views showing the novel tibial tubercle transfer procedure of the present invention being effected using still another novel form of apparatus.
Figure 47:
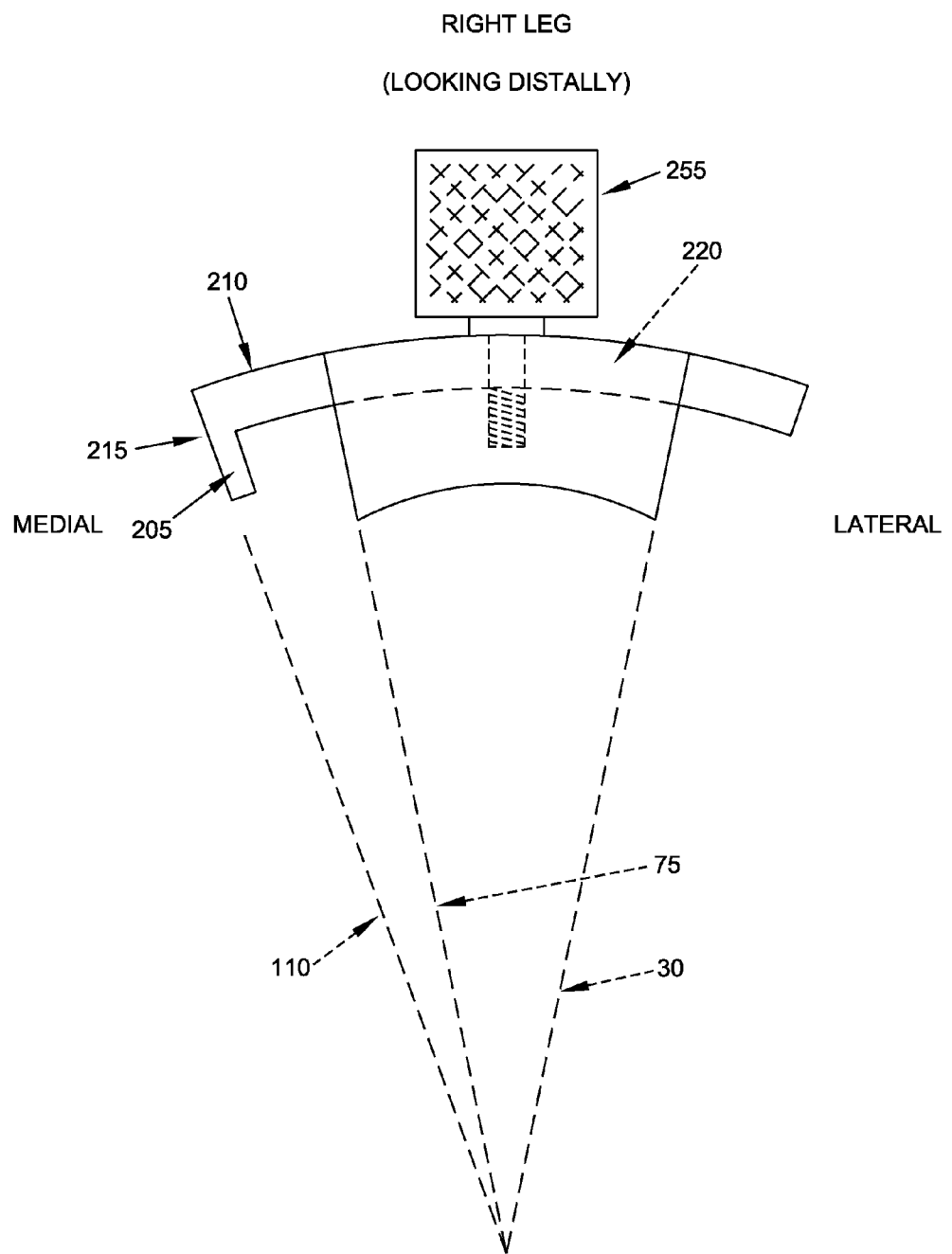

In accordance with another form of the present invention, and looking now at FIGS. 46 and 47, there is provided novel apparatus for effecting tibial tubercle transfer. This apparatus comprises the aforementioned jig 55 (with its aforementioned lateral edge 65 and its aforementioned cutting surface 80) and a novel sidearm 200. Sidearm 200 comprises an arm 205 connected to an arcuate guide 210. Arm 205 carries a flat saw guide 215. Arcuate guide 210 comprises an arcuate slot 220. A set screw 225, extending through arcuate slot 220 and into jig 55, is used to adjustably set the disposition of flat saw guide 215 relative to lateral edge 65 of jig 55 and cutting surface 80 of jig 55.

In use, jig 55 and sidearm 200 are used in the same manner as jig 55 and sidearm 100, i.e., lateral edge 65 of jig 55 is aligned with the first saw cut 30, cutting surface 80 of jig 55 is used to create second saw cut 75, and then flat saw guide 215 of sidearm 200 is used to create third saw cut 110. However, it will be appreciated that inasmuch as arcuate guide 210 comprises an arcuate slot 220, arcuate guide 210 can move across a larger range of motion while keeping flat saw guide aligned with distal point 85. As a result, a less robust set of sidearms is required in order to accommodate different degrees of offset for the third (medial) saw cut 110. This is a significant advantage, since it significantly reduces inventory requirements.

If desired, "dimensional" or "angular" markings 227 may be provided on arcuate guide 210, adjacent to arcuate slot 220, so show the surgeon how much the transfer is being effected by moving to a given position.

Sidearm With Cutting Slot

Figure 48:
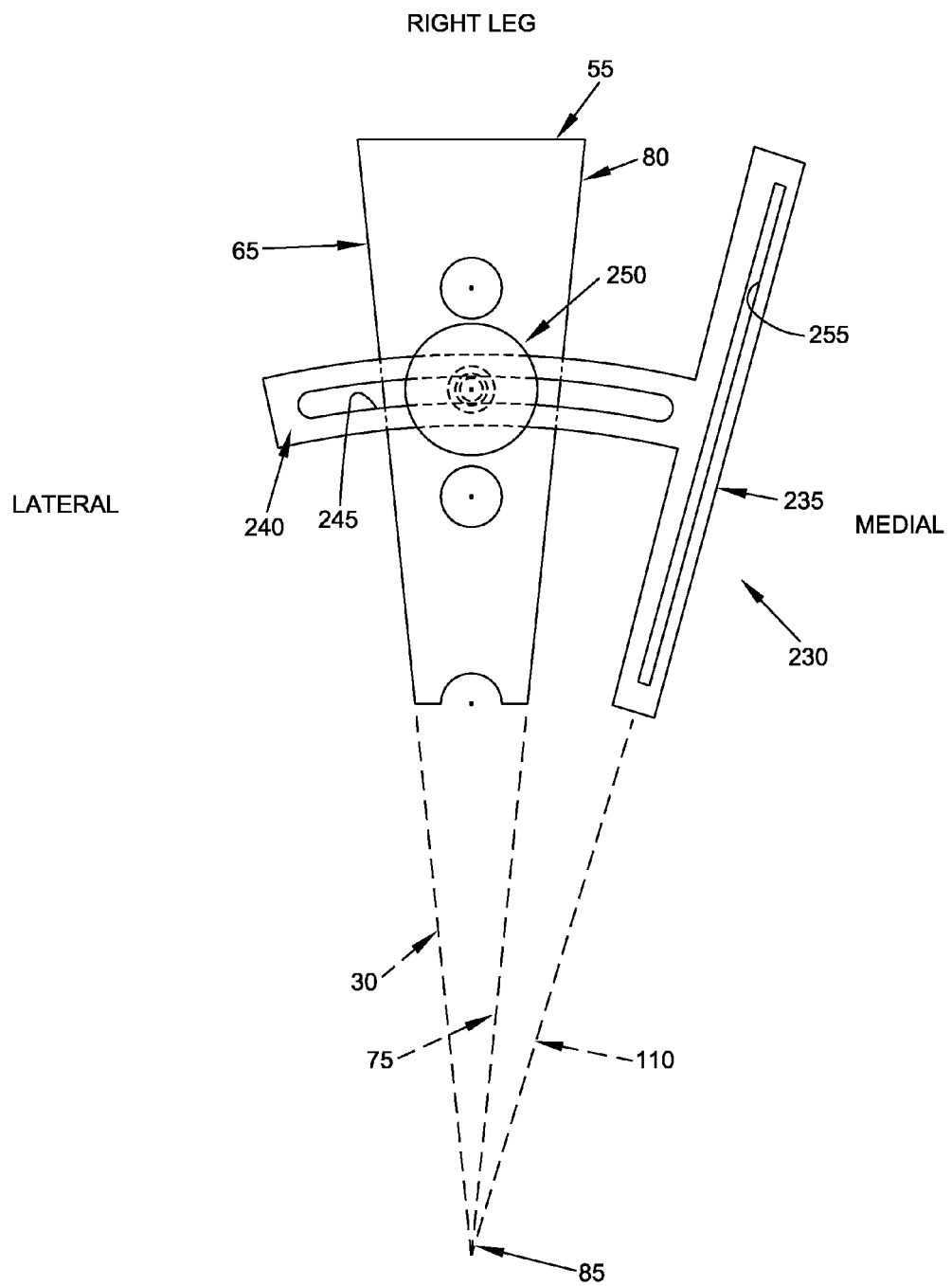
FIGS. 48 and 49 are schematic views showing the novel tibial tubercle transfer procedure of the present invention being effected using yet another novel form of apparatus.
Figure 49:
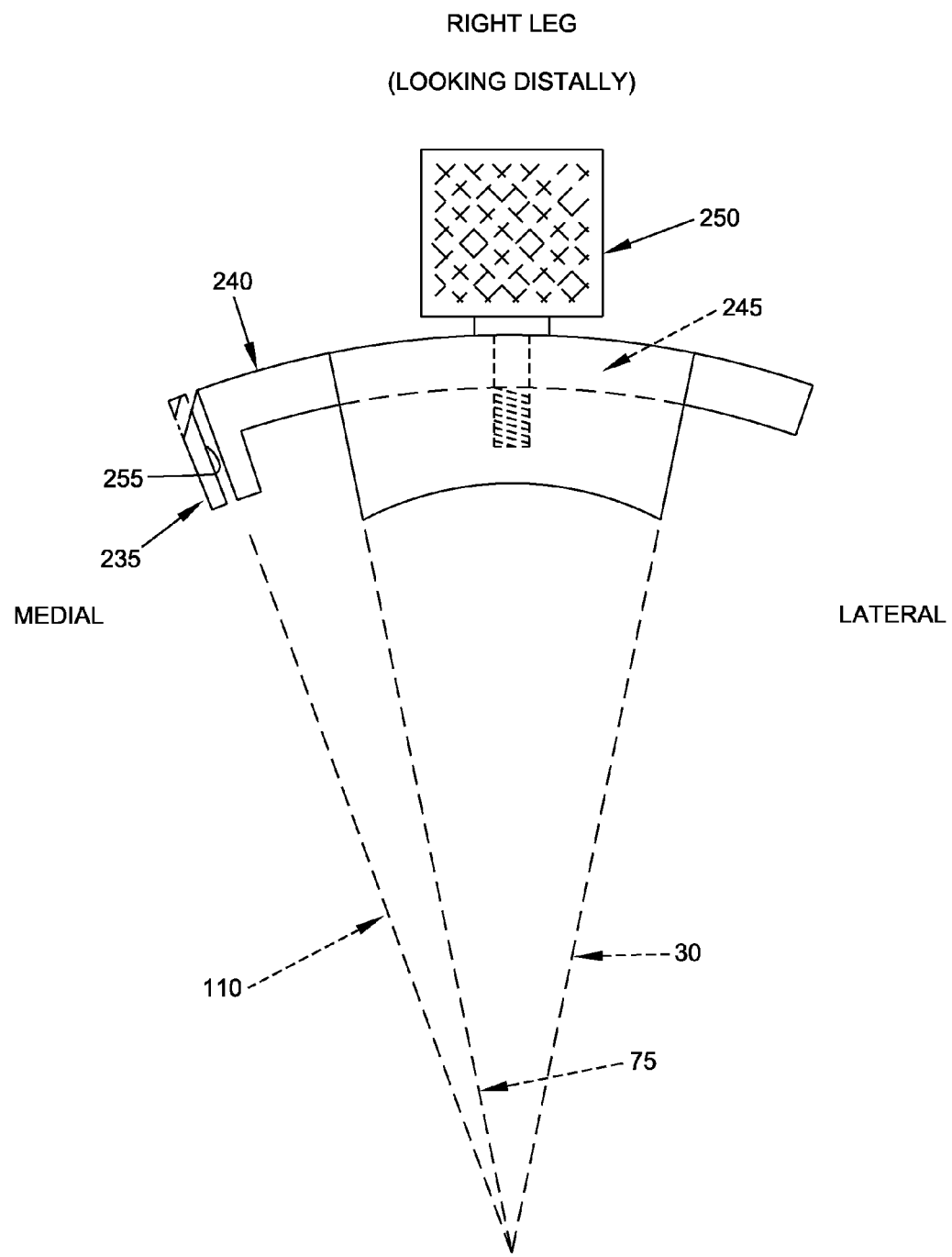

In another form of the invention, and looking next at FIGS. 48 and 49, the apparatus comprises the aforementioned jig 55 (with its aforementioned lateral edge 65 and its aforementioned cutting surface 80) and a novel sidearm 230. Sidearm 230 is substantially identical to the aforementioned sidearm 200 (i.e., it comprises an arm 235 connected to an arcuate guide 240, with arcuate guide 240 comprising an arcuate slot 245, and with a set screw 250 adjustably connecting sidearm 230 to jig 55). However, in this form of the invention, the flat saw guide 215 of sidearm 200 is replaced with a slot 255 formed in arm 235. Slot 255 forms a more constrained cutting guide for the surgeon, since it is bounded medial/lateral and proximal/distal. In some situations this can be more preferable than flat saw guide 235 of sidearm 200, which is primarily bounded medial/lateral.

Kit Comprising Jig, Medial Sidearm and Lateral Sidearm

In FIGS. 46 and 47, there is disclosed a jig 55 and a sidearm 200 for forming the bone cuts needed for the tibial tubercle transfer. In FIGS. 48 and 49, there is disclosed a jig 55 and a sidearm 230 for forming the bone cuts needed for the tibial tubercle transfer. In the case of jig 55 and sidearm 200, as well as in the case of jig 55 and sidearm 230, the size of the jig is related to the size of the bone wedges which are to be repositioned during the tibial tubercle transfer. Specifically, the disposition of lateral edge 65 and cutting surface 80 of jig 55 corresponds to the width of the bone block A which is to be cut from the tibia. As a result, in the form of the invention shown in FIGS. 46 and 47, and in the form of the invention shown in FIGS. 48 and 49, it is intended that jig 55 be provided in a range of different configurations so as to accommodate patients of different sizes. By way of example but not limitation, where the tibial tubercle transfer is to be effected on a relatively small patient, it is intended that jig 55 have its lateral edge 65 and cutting surface 80 arranged to set the distal point 85 relatively closer to jig 55, and where the tibial tubercle transfer is to be effected on a relatively large patient, it is intended that jig 55 have its lateral edge 65 and cutting surface 80 arranged to set the distal point 85 relatively farther from jig 55.

However, one consequence of this design is that a range of different jig configurations must be inventoried in order to accommodate patients of different sizes.

Figure 50:
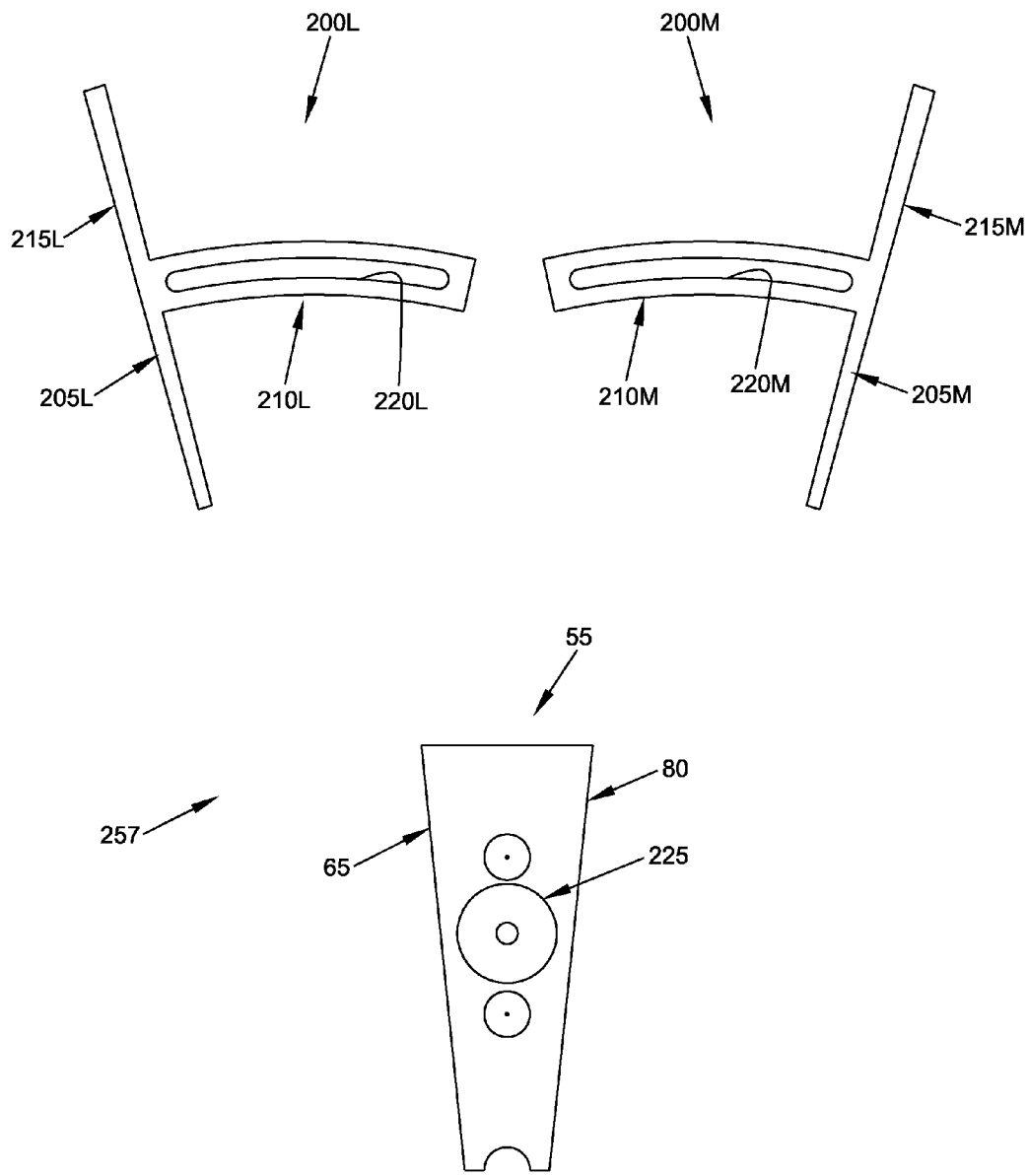
FIGS. 50-54 are schematic views showing the novel tibial tubercle transfer procedure of the present invention being effected using another novel form of apparatus.

Accordingly, in another form of the invention, and looking now at FIG. 50, there is provided a kit 257 which comprises the aforementioned jig 55 (with its aforementioned lateral edge 65 and its aforementioned cutting surface 80) and a pair of novel sidearms 200M and 200L. More particularly, jig 55 is constructed so that its lateral edge 65 and cutting surface 80 are configured for a relatively small patient, i.e., to set distal point 85 relatively closer to jig 55. Sidearm 200M (sometimes hereinafter referred to herein as a medial sidearm 200M) comprises an arm 205M connected to an arcuate guide 210M. Arm 205M carries a flat saw guide 215M. Arcuate guide 210M comprises an arcuate slot 220M. Sidearm 200L (sometimes hereinafter referred to herein as a lateral sidearm 200L) comprises an arm 205L connected to an arcuate guide 210L. Arm 205L carries a flat saw guide 215L. Arcuate guide 210L comprises an arcuate slot 220L. A set screw 225, extending through arcuate slot 220M in medial sidearm 200M and into jig 55, or extending through arcuate slot 220L in lateral sidearm 200L and into jig 55, is used to adjustably set the disposition of flat saw guide 215M of medial sidearm 200M, or flat saw guide 215L of lateral sidearm 200L, relative to lateral edge 65 of jig 55 and cutting surface 80 of jig 55.

Figure 51:
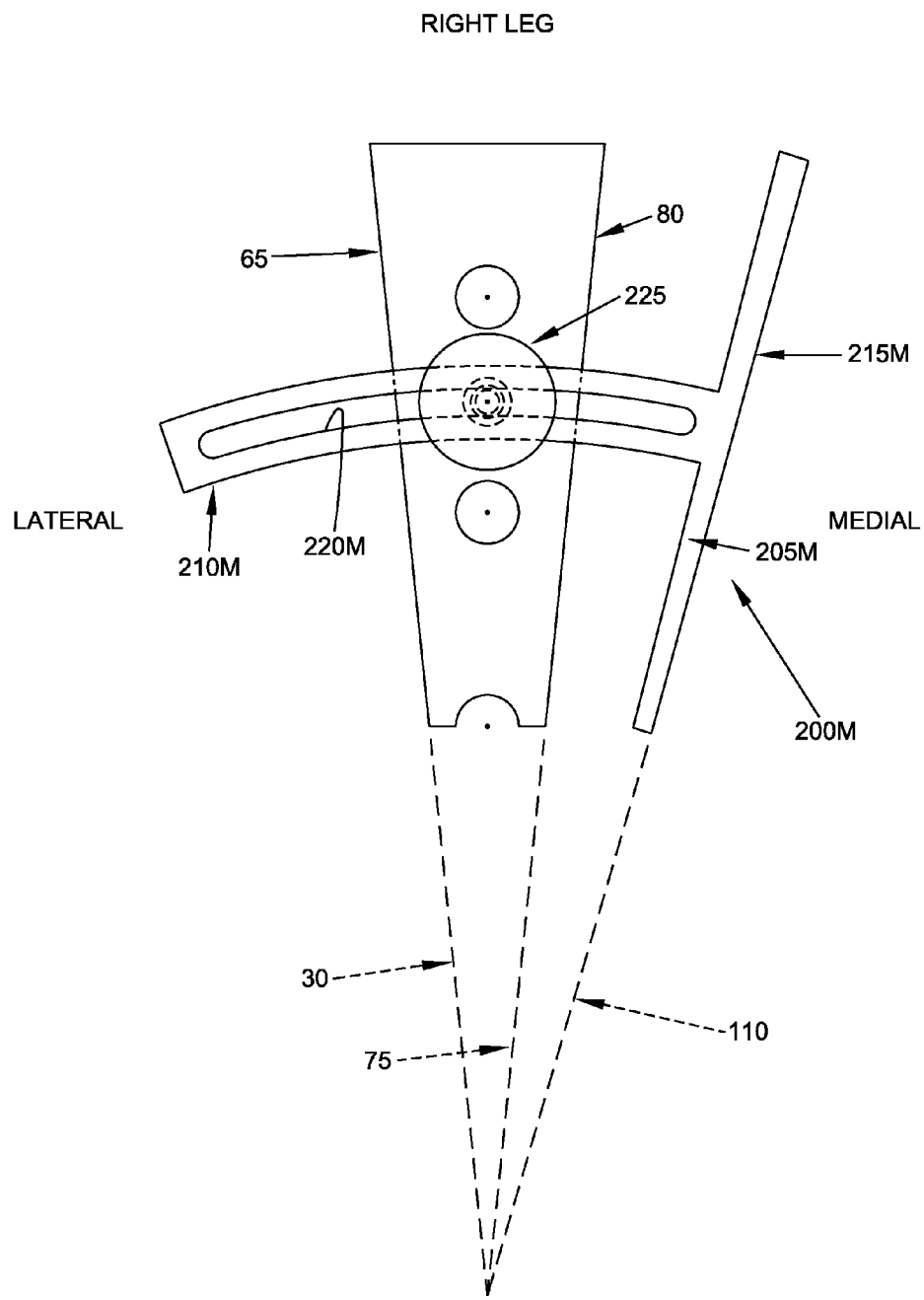

In use, jig 55 is positioned against the patient. If it appears to the surgeon that jig 55 is appropriately sized for that particular patient, then the surgery proceeds in a manner analogous to that described above, i.e., first saw cut 30 is created, jig 55 is secured in position against the tibia, cutting surface 80 of jig 55 is used to create second saw cut 75, and then flat saw guide 215M of sidearm 200M is used to create third saw cut 110. See FIG. 51.

Figure 52:
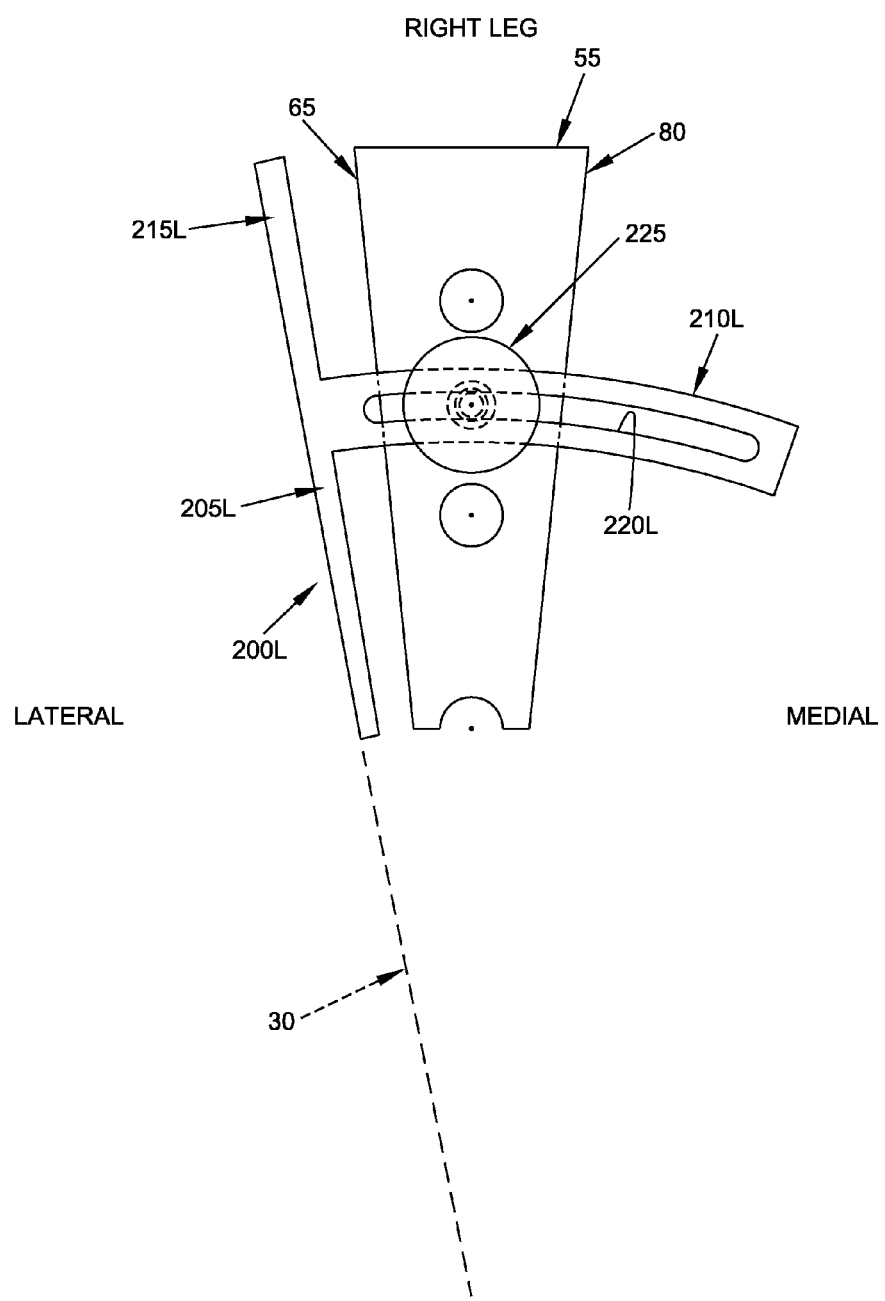
Figure 53:
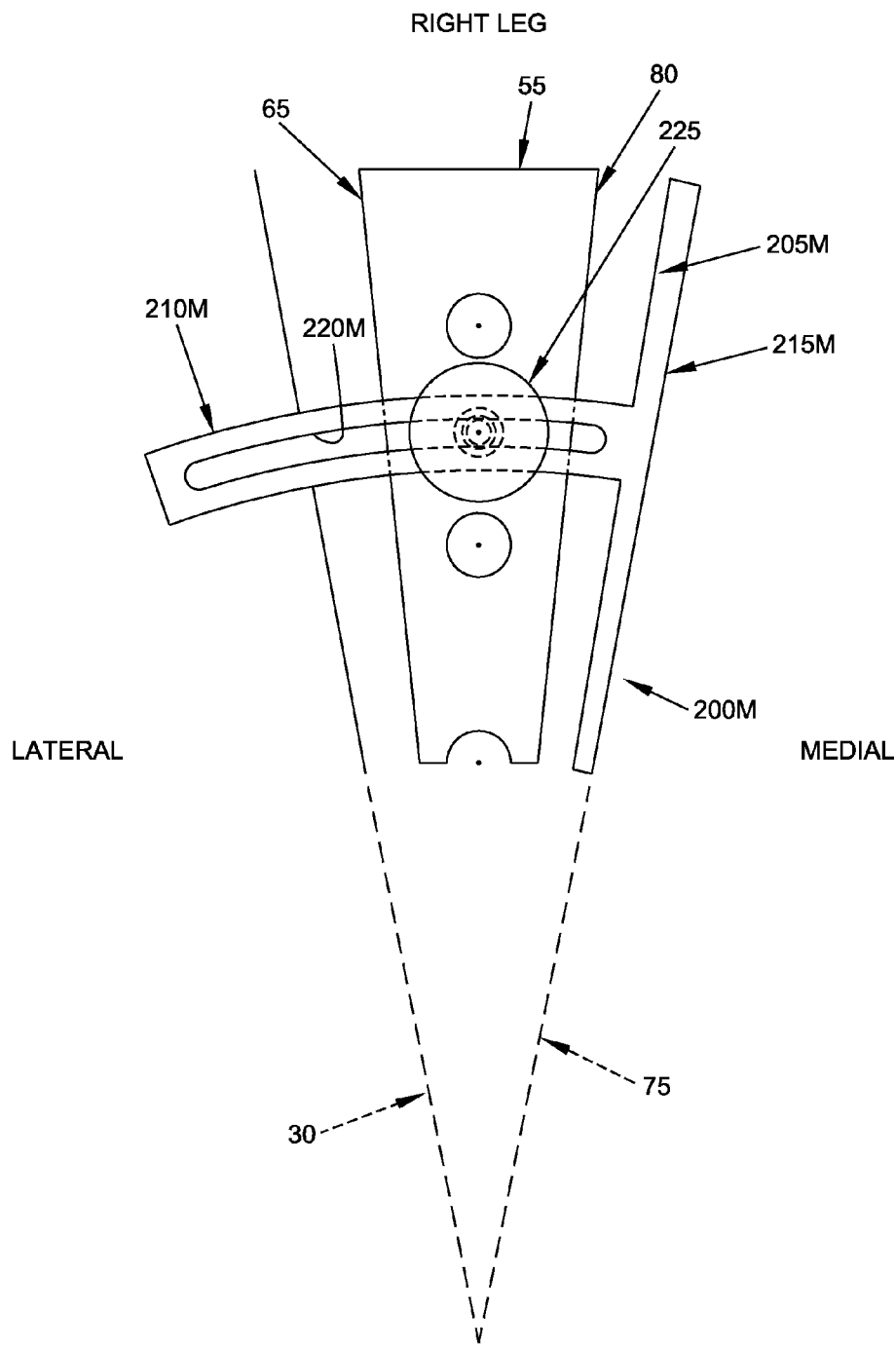
Figure 54:
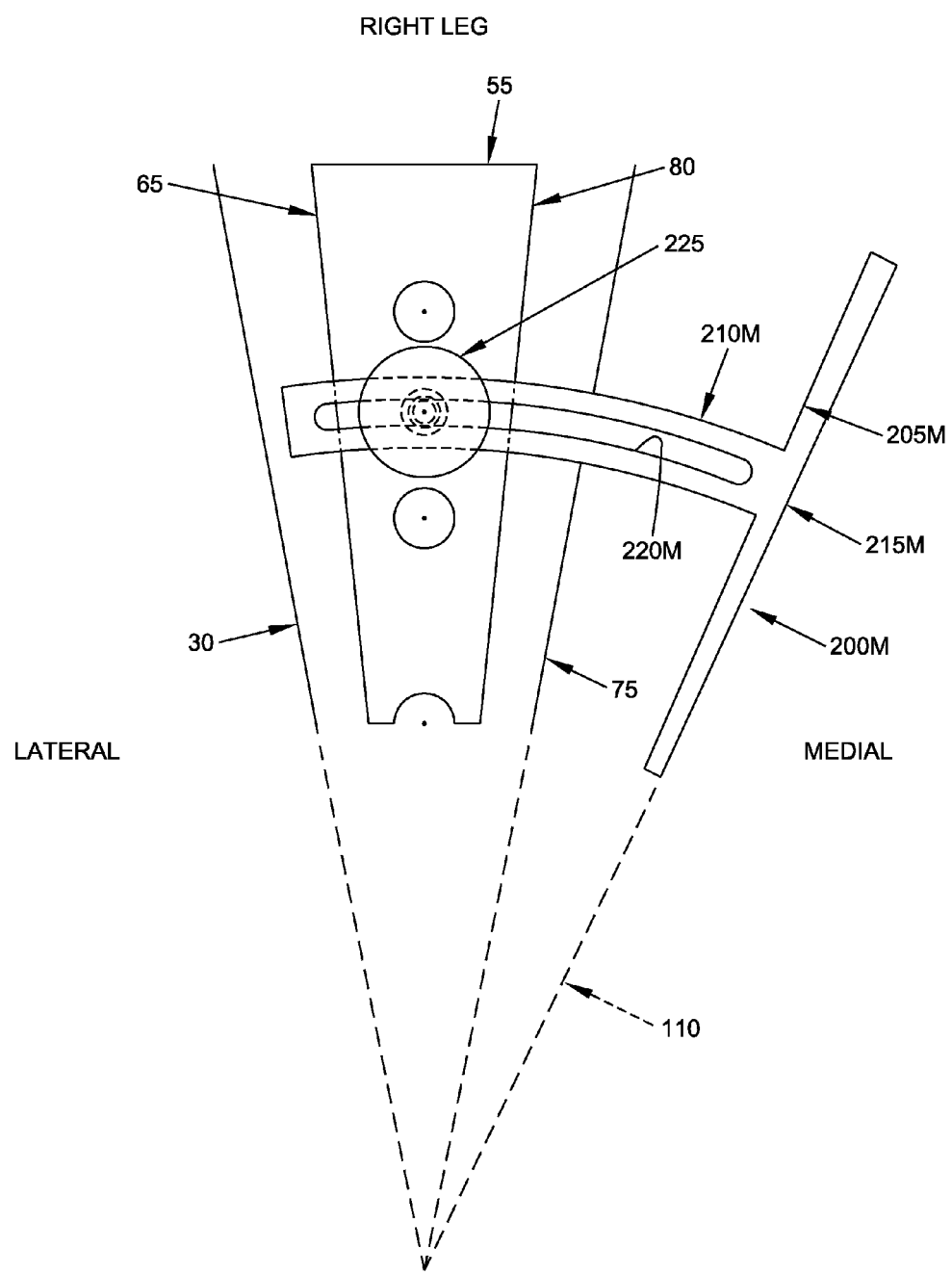
Figure 55:
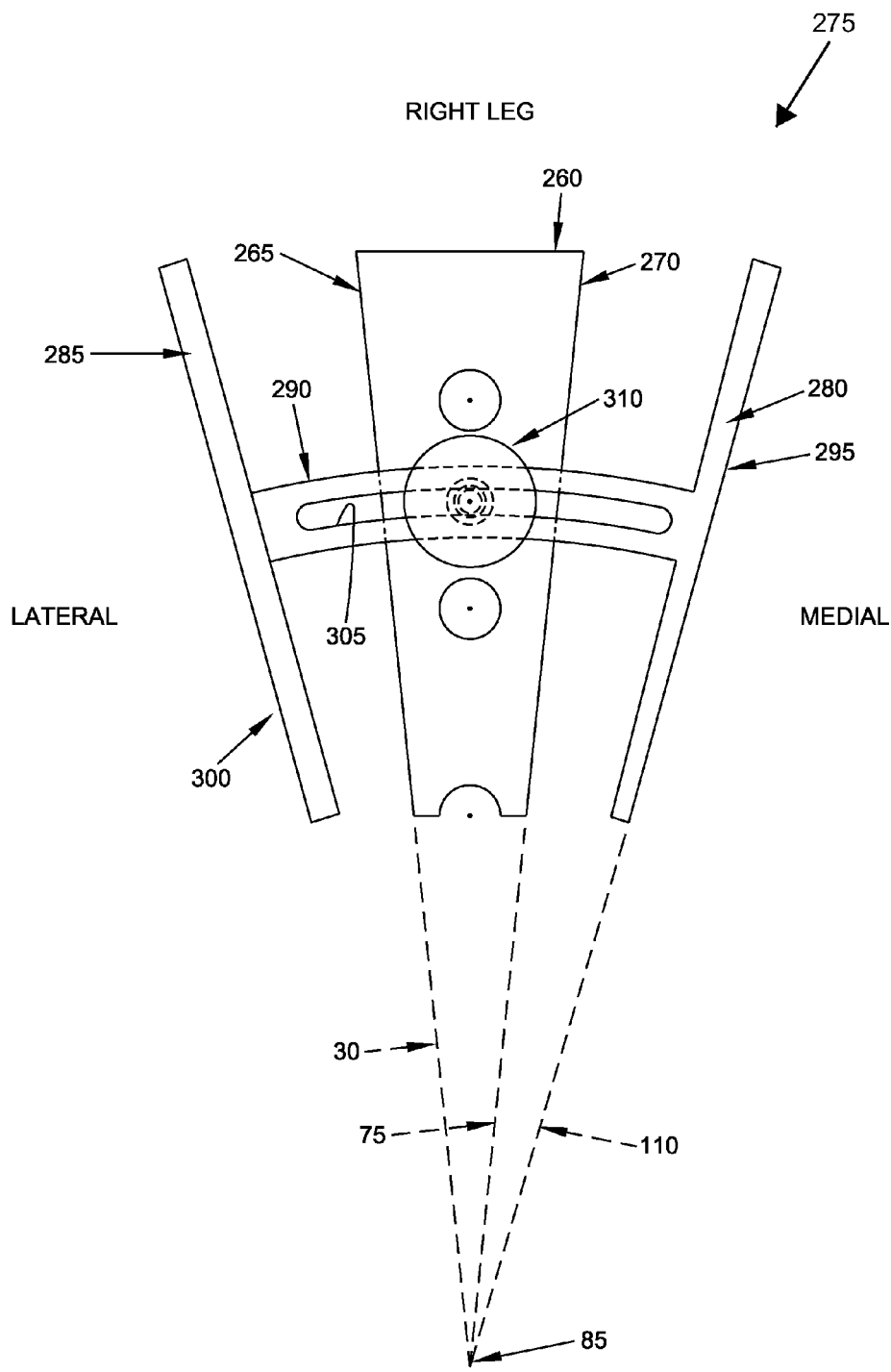
FIGS. 55-58 are schematic views showing the novel tibial tubercle transfer procedure of the present invention being effected using still another novel form of apparatus.
Figure 56:
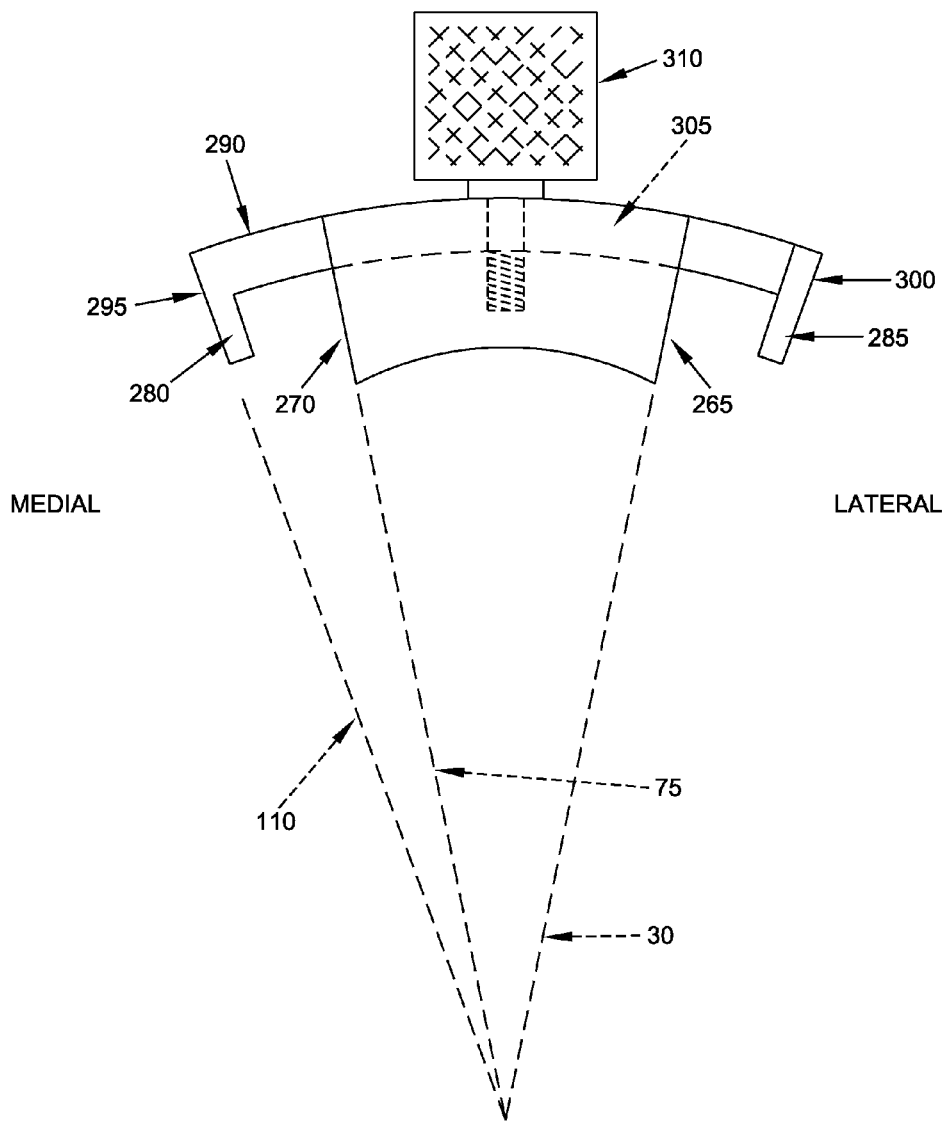
Figure 57:
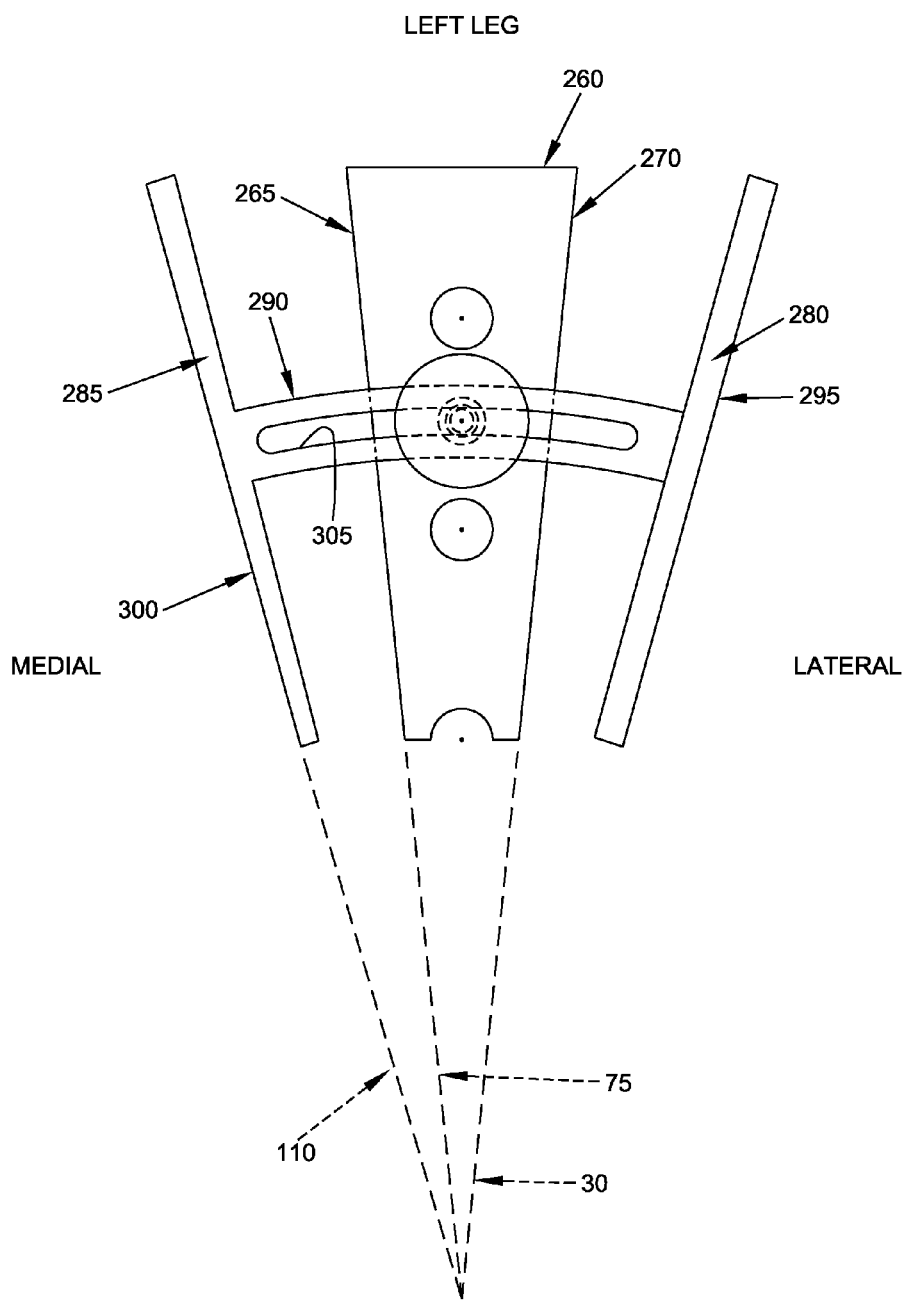
Figure 58:
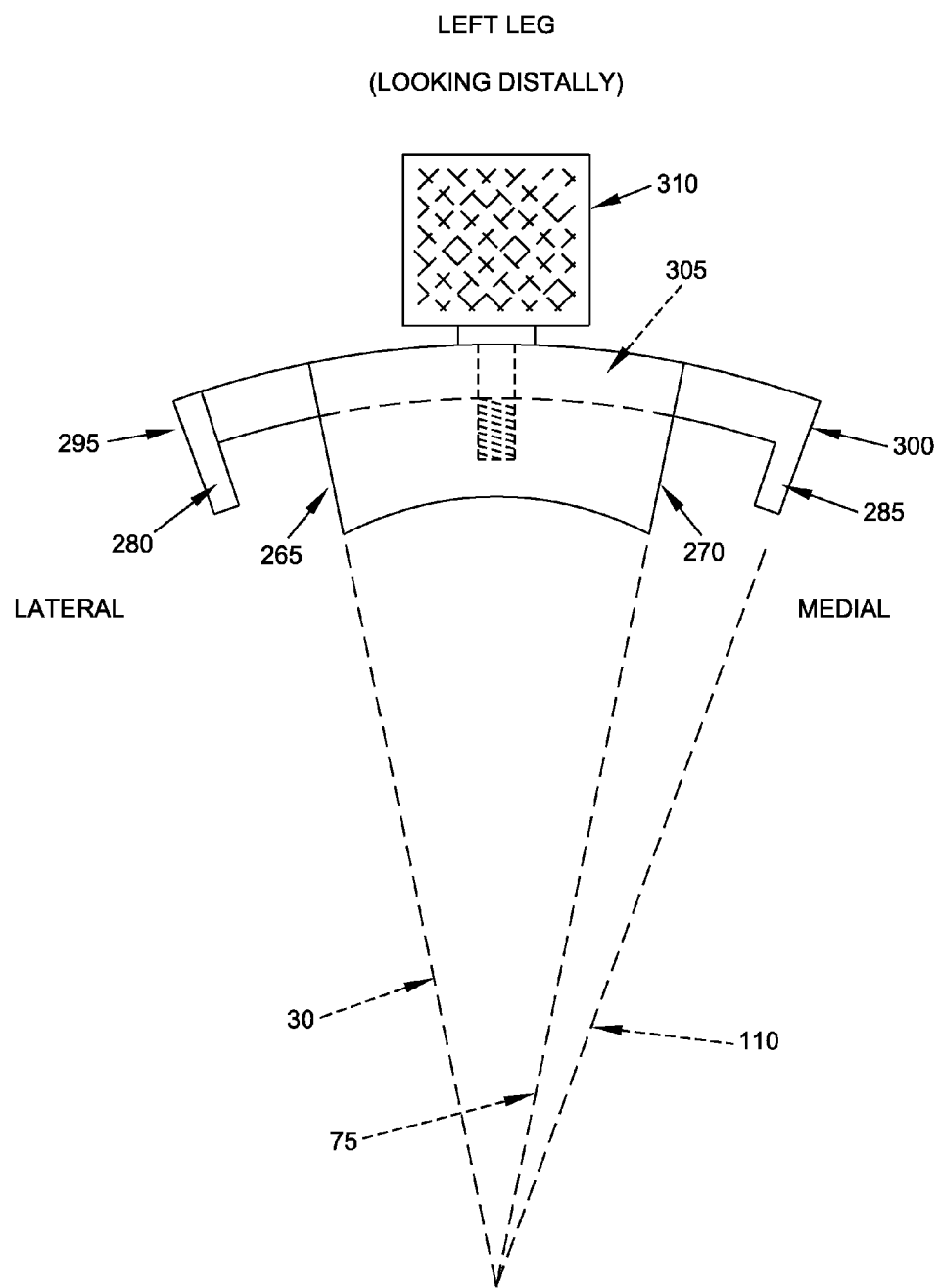

However, in the event that the surgeon determines that jig 55 is "too small" for that particular patient, the surgeon mounts jig 55 to the patient, loosely mounts lateral sidearm 200L on the jig, sets the position of flat saw guide 215L to the appropriate location, secures the lateral sidearm to the jig using set screw 225, and then cuts first saw cut 30 using flat saw guide 215L. See FIG. 52. Then the surgeon removes lateral sidearm 200L from the jig and replaces it with medial sidearm 200M. The surgeon adjusts the position of medial sidearm 200M so that flat saw guide 215M is set to the appropriate location to form second saw cut 75, secures the medial sidearm to the jig using the set screw 225, and then cuts second saw cut 75. See FIG. 53. Then the surgeon loosens set screw 225, adjusts the position of medial sidearm 200M so that flat saw guide 215M is set to the appropriate location to form third saw cut 110, secures the medial sidearm 200M to the jig using the set screw 225, and then cuts third saw cut 110. See FIG. 54.

Thus it will be seen that by providing a kit 257 consisting of a jig 55, a medial sidearm 200M and a lateral sidearm 200L, patients of different sizes can be treated using a single jig.

Symmetrical Sidearm

In another form of the invention, and looking now at FIGS. 55-58, the apparatus for effecting a tibial tubercle transfer comprises a jig 260 which comprises a first surface 265 and a second surface 270, and a symmetrical sidearm 275 which comprises a first arm 280 and a second arm 285, with first arm 280 being connected to second arm 285 with an arcuate guide 290. First arm 280 carries a first flat saw guide 295 and second arm 285 carries a second flat saw guide 300. Arcuate guide 290 comprises an arcuate slot 305. A set screw 310, extending through arcuate slot 305 and into jig 260, is used to adjustably set the disposition of first flat saw guide 295 of arcuate guide 290 and second flat saw guide 300 of arcuate guide 290 relative to first surface 265 of jig 260 and second surface 270 of jig 260.

In use, when a tibial tubercle transfer is to be effected on the right leg of a patient, and where jig 55 is determined to be of the appropriate size for the patient, first surface 265 of jig 260 is aligned with the first saw cut 30, second surface 270 of jig 260 is used to create second saw cut 75, and then first flat saw guide 295 of arcuate guide 290 is used to create third saw cut 110. See FIGS. 55 and 56.

Correspondingly, when a tibial tubercle transfer is to be effected on the left leg of a patient, and where jig 55 is determined to be of the appropriate size for the patient, second surface 270 of jig 260 is aligned with the first saw cut 30, first surface 265 of jig 260 is used to create second saw cut 75, and then second flat saw guide 300 of arcuate guide 290 is used to create third saw cut 110. See FIGS. 57 and 58.

Thus it will be seen that with the apparatus of jig 260 and symmetrical sidearm 275, exactly the same apparatus can be used to perform both a right leg tibial tubercle transfer and a left leg tibial tubercle transfer. This is a significant advantage, since it significantly reduces inventory requirements.

In addition to the foregoing, with the apparatus of jig 260 and symmetrical sidearm 275, if it should be determined that jig 260 is too small for the patient, it is possible to form both lateral and medial bone cuts with the single symmetrical sidearm 275.

Thus, in this approach, one of the flat saw guides 295, 300 of symmetrical sidearm 275 is used to create the first bone cut 30, then the other of the flat saw guides 295, 300 of symmetrical sidearm 275 is used to create the second bone cut 75, symmetrical sidearm 275 is moved medially, and then the same one of the flat saw guides 295, 300 of symmetrical sidearm 275 is used to create the third saw cut 110. Specifically, if the tibial tubercle transfer is to be effected on the right leg of the patient, second flat saw guide 300 of symmetrical sidearm 275 is used to create the first saw cut 30, first flat saw guide 295 of symmetrical sidearm 275 is used to create second saw cut 75, symmetrical sidearm 275 is moved medially and first flat saw guide 295 of symmetrical sidearm 275 is used to create third saw cut 110. Conversely, if the tibial tubercle transfer is to be effected on the left leg of the patient, first flat saw guide 295 of symmetrical sidearm 275 is used to create the first saw cut 30, second flat saw guide 300 of symmetrical sidearm 275 is used to create second saw cut 75, symmetrical sidearm 275 is moved medially, and second flat saw guide 300 of symmetrical sidearm 275 is used to create third saw cut 110. In this way, by using symmetrical sidearm 275 to create all three of the bone cuts in a tibial tubercle transfer procedure, the configuration of jig 260 can be independent of the size of the bone blocks which are to be created. As a result, inventory requirements can be minimized.

Materials And Packaging

It will be appreciated that any of the aforementioned jigs, shims and/or sidearms may be reusable or disposable, and may be constructed from metal, plastic, etc. as appropriate. Furthermore, if desired, disposable components may be provided in sterile-packaged condition so that no autoclaving is required.

Modifications

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for performing a multidirectional tibial tubercle transfer, the method comprising:
    providing an apparatus comprising:
        a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and
        an extender for attaching to the jig, wherein the extender comprises a third guide surface, wherein the third guide surface simultaneously converges towards the point of convergence of the first and second guide surfaces of the jig as the third guide surface extends (i) distally down the tibia, and (ii) posteriorly towards the tibia;
        wherein the extender comprises an arcuate slot, and further wherein the extender is attached to the jig by means of the arcuate slot;
    making a first cut in the tibia;
    aligning the first guide surface of the jig with the first cut in the tibia;
    making a second cut in the tibia using the second guide surface of the jig; and
    making a third cut in the tibia using the third guide surface of the extender.

2. A method for performing a multidirectional tibial tubercle transfer, the method comprising:
    providing an apparatus comprising:
        a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and
        an extender for attaching to the jig, wherein the extender comprises a third guide surface, wherein the third guide surface simultaneously converges towards the point of convergence of the first and second guide surfaces of the jig as the third guide surface extends (i) distally down the tibia, and (ii) posteriorly towards the tibia;
        wherein the extender comprises a slot, and further wherein the third guide surface defines a portion of the slot;
    making a first cut in the tibia;
    aligning the first guide surface of the jig with the first cut in the tibia;
    making a second cut in the tibia using the second guide surface of the jig; and
    making a third cut in the tibia using the third guide surface of the extender.

3. A method for performing a multidirectional tibial tubercle transfer, the method comprising:
    providing an apparatus comprising:
        a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia;
        a medial extender for attaching to the jig, wherein the medial extender comprises a third guide surface, wherein the third guide surface is directed towards a point distal to the point of convergence of the first and second guide surfaces of the jig as the third guide surface extends (i) distally down the tibia, and (ii) posteriorly towards the tibia; and
        a lateral extender for attaching to the jig, wherein the lateral extender comprises a fourth guide surface, wherein the fourth guide surface is directed towards a point distal to the point of convergence of the first and second guide surfaces of the jig as the fourth guide surface extends (i) distally down the tibia, and (ii) posteriorly towards the tibia;
    determining if the jig is appropriately sized for the patient;
    if it is determined that the jig is appropriately sized for the patient, making a first cut in the tibia, aligning the first guide surface of the jig with the first cut in the tibia, making a second cut in the tibia using the second guide surface of the jig, and making a third cut in the tibia using the third guide surface of the medial extender;
    if it is determined that the jig is not appropriately sized for the patient, making a first cut in the tibia using the fourth guide surface of the lateral extender, making a second cut in the tibia using the third guide surface of the medial extender, and making a fourth cut in the tibia using the third guide surface of the medial extender.

4. A method for performing a multidirectional tibial tubercle transfer, the method comprising:
    providing an apparatus comprising:
        a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and
        an extender for attaching to the jig, wherein the extender comprises a third guide surface and a fourth guide surface, wherein the third guide surface and the fourth guide surface simultaneously converge towards the point of convergence of the first and second guide surfaces of the jig as the third guide surface and the fourth guide surface extend (i) distally down the tibia, and (ii) posteriorly towards the tibia;
    making a first cut in the tibia;
    aligning the first guide surface of the jig with the first cut in the tibia;

making a second cut in the tibia using the second guide surface of the jig; and making a third cut in the tibia using the third guide surface of the extender.

5. A method for performing a multidirectional tibial tubercle transfer, the method comprising:
 providing an apparatus comprising:
  a jig for positioning against the anterior portion of the tibia, the jig comprising first and second guide surfaces, wherein the first and second guide surfaces simultaneously converge towards one another as they extend (i) distally down the tibia, and (ii) posteriorly towards the tibia; and
  an extender for attaching to the jig, wherein the extender comprises a third guide surface and a fourth guide surface, wherein the third guide surface and the fourth guide surface simultaneously converge towards a point distal to the point of convergence of the first and second guide surfaces of the jig as the third guide surface and the fourth guide surface extend (i) distally down the tibia, and (ii) posteriorly towards the tibia;
 making a first cut in the tibia using the fourth guide surface of the extender;
 making a second cut in the tibia using the third guide surface of the extender; and
 making a third cut in the tibia using the third guide surface of the extender.

* * * * *